United States Patent [19]

Middendorf et al.

[11] Patent Number: 5,207,880

[45] Date of Patent: May 4, 1993

[54] DNA SEQUENCING

[75] Inventors: Lyle R. Middendorf; John A. Brumbaugh, both of Lincoln, Nebr.

[73] Assignee: The Board of Regents of the University of Nebraska, Lincoln, Nebr.

[21] Appl. No.: 570,503

[22] Filed: Aug. 21, 1990

Related U.S. Application Data

[60] Continuation-in-part of Ser. No. 78,279, Jul. 27, 1987, abandoned, which is a division of Ser. No. 594,676, Mar. 29, 1984, Pat. No. 4,729,947.

[51] Int. Cl.$^5$ .................... G01N 27/26; B01D 57/02
[52] U.S. Cl. .............................. 204/182.8; 204/299 R
[58] Field of Search ............. 204/299 R, 182.8, 180.1

[56] References Cited

U.S. PATENT DOCUMENTS

3,533,933  10/1970  Strauch ........................... 204/182.8

FOREIGN PATENT DOCUMENTS

2303846  8/1974  Fed. Rep. of Germany ... 204/299 R

OTHER PUBLICATIONS

Roberto Cotrufo, "High Sensitivity Method for Fluorofore Detection in Gradient Polyacrylamide Slab Gels through Excitation by Laser Light: Application to Glycoproteins Stained with Concanavalin A-Fluorescein Isothiocyanate", Analytical Biochemistry 134 (1983) 313-319.

J. E. Brayden & W. Halpern, "A High-Spatial-Resolution Laser Beam Densitometer for Quantitative Analysis of Polyacrylamide Gels", Analytical Biochemistry 130 (1983) 9-13.

John J. Kopchick et al., "Rapid Analysis of Small Nucleic Acid Samples by Gel Electrophoresis", Analytical Biochemistry 115 (1983) 419-423.

Piotr Naimski et al., "Quantitative Analysis of Different Conformational Forms of DNA Bound to the Dye, 4'6-Diomidine-2-phenylindole, and Separated by Gel Electrophoresis", Analytical Biochemistry 106 (1980) 471-475.

B. C. Hyman & T. W. James, "Detection of A & T-Rich DNA in Gels by Differential Fluorescence", Analytical Biochemistry 131 (1983) 205-210.

U. Möller et al., "Evaluation of Stained and Unstained Electropherograms by Photoacoustic Spectroscopy", Journal de Physique, Colleague C6 (1983) C6121-C6124.

U. Möller et al., "Evaluation of Electrophoregrams by Means of Photoacoustic Spectrosopy", Journal of Photoacoustics, 1(2) (1982) 309-316.

*Primary Examiner*—John Niebling
*Assistant Examiner*—John S. Starsiak
*Attorney, Agent, or Firm*—Vincent L. Carney

[57] ABSTRACT

To sequence DNA automatically, flourescently marked DNA are electrophoresed in a plurality of channels through a gel electrophoresis slab; wherein the DNA samples are resolved in accordance with the size of DNA fragments in the gel electrophoresis slab into fluorescently marked DNA bands. The separated samples are scanned photoelectrically with a laser and a sensor, wherein the laser scans with scanning light at a scanning light frequency within the absorbance spectrum of said fluorescently marked DNA samples and light is sensed at the emission frequency of the marked DNA. The light is modulated from said laser at a predetermined modulation frequency and fluorescent light emitted by said DNA bands at said modulation frequency is detected, whereby background noise from the medium through which the light is transmitted is discriminated against.

12 Claims, 13 Drawing Sheets

DNA SEQUENCING

REFERENCE TO RELATED APPLICATIONS

This application is a continuation-in-part application of 07/078,279 filed Jul. 27, 1987, now abandoned which is a division of United States application Ser. No. 594,676 for DNA SEQUENCING filed by Middendorf et al. on Mar. 29, 1984, and assigned to the same assignee as this application, now U.S. Pat. No. 4,729,947.

BACKGROUND OF THE INVENTION

This invention relates to the sequencing of DNA strands.

In one class of techniques for sequencing DNA, identical strands of DNA are marked. The strands are separated into four aliquots. The strands in a given aliquot are either individually cleaved at or synthesized to any base belonging to only one of the four base types, which are adenine, guanine, cytosine and thymine (hereinafter A, G, C and T). The adenine-, guanine-, cytosine- and thymine-terminated strands are then electrophoresed for separation. The rate of electrophoresis indicates the DNA sequence.

In a prior art sequencing technique of this class, the DNA strands are marked with a radioactive marker, cleaved at any base belonging to a base type unique to the aliquot in which the strands are contained, and after being separated by electrophoresis, film is exposed to the gel and developed to indicate the sequence of the bands. The range of lengths and resolution of this type of static detection is limited by the size of the apparatus.

In another prior art sequencing technique of this class, single strands are synthesized to any base belonging to a base type unique to the aliquot in which the strands are contained. The strands are marked radioactively for later detection.

It is also known in the prior art to use fluorescent markers for marking proteins and to pulse the fluorescent markers with light to receive an indication of the presence of a particular protein from the fluorescence.

The prior art techniques for DNA sequencing have several disadvantages such as: (1) they are relatively slow; (2) they are at least partly manual; and (3) they are limited to relatively short strands of DNA.

In a technique related to DNA sequencing, used to identify restriction fragment length polymorphisms (RFLPs), DNA strands, cut by restriction enzymes, are separated into bands by electrophoresis and moved at right angles onto a blotting matrix containing radioactively labelled probes for identification. This procedure has the same disadvantages as the prior art sequencing procedures.

SUMMARY OF THE INVENTION

Accordingly, it is an object of the invention to provide a novel technique for DNA sequencing.

It is a still further object of the invention to provide novel apparatuses and methods for sequencing relatively large fragments of DNA.

It is a still further object of the invention to provide novel apparatuses and methods for sequencing DNA fragments of 100 bases or more.

It is a still further object of the invention to provide a technique for continuous sequencing of DNA.

It is a still further object of the invention to continuously sequence DNA without the spatial limitations of range of lengths and resolution.

It is a still further object of the invention to provide a novel technique for continuously sequencing DNA using fluorescent detection.

It is a still further object of the invention to provide a novel technique for DNA sequencing using a fluorescent marker fastened to the DNA, or the inherent fluorescence of the DNA itself.

It is a still further object of the invention to provide a novel technique for continuously sequencing DNA marked with fluorescence which more clearly distinguishes marked DNA fragments from background fluorescence.

It is a still further object of the invention to provide a novel technique for continuously sequencing DNA using radioactive detection.

In accordance with the above and further objects of the invention, strands of DNA are continuously electrophoresed and identified for: (1) DNA sequencing; and (2) analysis of strands varying in length, as prepared by such techniques as restriction enzyme cutting or polymerase chain reaction (PCR), and marked by direct labelling of fluorescent markers to the strands or by fluorescently labelled probes hybridized to the separated strands. The strands are fluorescently marked and the light emitted during a scan is detected and correlated. The gel and voltage are selected so that strands being electrophoresed near the terminal end of the gel channel are fully resolved prior to the resolution of longer strands which are at the entrance end of the gel channel, and so on, in a continuous process over a period of time.

One embodiment of apparatus for sequencing DNA includes at least four electrophoresis channels, each adapted to receive fluorescently labeled DNA strands, having at one end a base of a given type. Each of the channels has a gel path and electrical field across it identical in its characteristics to the gel path of the other channels and electrical fields across the other channels.

To provide marking in one embodiment, a fluorescent marker is attached to the DNA fragments prior to their being electrophoresed into the gel. In another embodiment, probes are used to combine or hybridize with the DNA strands, with detection accomplished by detecting a fluorescent marker that is chemically attached to the probe. In the preferred embodiment, the marker is a dye that fluoresces in the infrared or near infrared region.

In another embodiment, biotin is attached to the DNA fragments prior to their being electrophoresed into the gel and at the terminal end of the gel, avidin is applied to the strands to further mark the strands individually while maintaining the strands in each channel separate from the strands in other channels. The avidin is pre-marked with multiple fluorescent molecules and therefore provides multiple fluorescent markers for each separated strand.

In other embodiments, after separation: (1) the inherent fluorescence of DNA is used as a suitable detection mechanism, so that it is not necessary to mark one end of the strands with biotin nor mark them with a fluorescent marker nor attach fluorescently labelled primers; or (2) radioactive markers attached directly to the DNA are used as a suitable detection mechanism.

The gel electrophoresis may be provided in conventional gel slabs. In one embodiment, there is a different input section for each of four channels that are for a corresponding one of the A, G, T and C strands.

As alternatives to a gel slab: (1) four capillary tubes may be used with gel in them to allow higher voltages per unit length of the gel without excess heating, thereby allowing faster separation; (2) open capillary tubes may be used and thus avoid the need for gel and make the cleaning more convenient; (3) high performance liquid chromatography (HPLC) columns such as ion-exchange columns or reverse phase columns may be used in conjunction with pressure instead of voltage for separating the strands; or (4) fewer or more four channels may be used with or without marking that separates the DNA strands.

The strands are detected during electrophoresis either in the gel or after leaving the gel by scanning back and forth across the gel at a fixed distance from the entrance end of the gel or by moving the strands by bulk flow, such as through the use of a moving blotting membrane past a detector or detectors. Means are provided for detecting the bands individually in each channel in accordance with their mobility in the gel to indicate the sequence of the A, G, C and T strands of different lengths. Advantageously, an additional channel may be utilized as a calibration channel through the electorphoresis of DNA strands of known, but different lengths. These DNA strands are also marked and thereby indicate a time base.

The scanning apparatus includes a light source, such as a laser or arc lamp or other suitable source that emits light in the optimum absorption spectrum of the marker. The light may be split by the use of fiber. In the preferred embodiment, the light source is a diode laser that scans the channels with infrared light having a wave length that matches the absorbance region of the marker. The detector includes a light sensor which is preferably an avalanche photodiode sensitive to the near infrared light emission of the marker. It may include a filtering system having a band pass suitable for passing selectively the optimum emission of the fluorescent marker to the light sensor.

The photodiode, photomultiplier or other light detector selectively detects the fluorescence using techniques which enhance the signal/noise ratio. One technique is to modulate the laser source by pulsing the electrical current driving the laser, with detection through a lock-in amplifier.

Another technique is the use of laser pulses which are less than five nanoseconds time duration, with detection in a time window. The length of such window and its delay from the pulse are optimized to discriminate against background fluorescence.

Correlation with the channel in which the fluorescent light is detected with the time of detection indicates: (1) if the type of base termination or nucleotide cleavage is A, G, C or T; and (2) the time sequence of separation of each strand in each channel of the electrophoresis gel column to indicate the overall sequence of strands.

To use the apparatus to sequence DNA strands, identical DNA strands are normally formed of a length greater than 100 bases. In one embodiment, the strands are marked by a suitable marker at one end. The strands are divided into four aliquots and the strands within each aliquot are cleaved at any base belonging to a specific base type. In another embodiment, strands are synthesized to any base belonging to a specific base type. These four aliquots are then electrophoresed through identical channels to separate strands so that the shorter strands are resolved towards the end of the gel prior to resolution of the longer strands, which still are near the entrance end of the gel. This occurs in a continuous process so a substantial number of different length strands may be resolved in a relatively short gel. This methodology takes advantage of time-resolved bands, as opposed to the limitations of spatial-resolved bands.

The gel size, electric field and DNA mobilities are such that the more mobile bands are fully resolved while the less mobile bands are yet unresolved in a continuous process such that at least ten percent of the bands have been resolved by electrophoresis in the gel while the less mobile bands which are near the entrance end of the gel are not fully resolved. These less mobile bands become resolved little by little over time in a continuous fashion without interruption of the movement of these bands through the gel.

The markers are detected by transmitting light to the markers. In the preferred embodiment, light is transmitted to a fluorescent marked DNA strand. In the latter case, the fluorescent light is detected either by modulating the light source and detecting using lock-in techniques or detecting during a time period in which the markers' fluorescence has not yet decayed to an insignificant amount but the background fluorescence has. The detection is made in a wavelength band including the high emission spectrum of the fluorescent marker.

For the gated window technique, the light is transmitted from pulsed lasers in approximately three nanosecond pulses. Readings are taken within a window period, after an initial delay, and both period and delay are optimized for best results. In another embodiment, radioactive marked strands, after being separated, excite a phosphor or scintillation liquid whereby detection of the presence of the strands is accomplished by an appropriate photodetector.

From the above summary, it can be understood that the sequencing techniques of this invention have several advantages, such as: (1) they take advantage of resolution over time, as opposed to space; (2) they are continuous; (3) they are automatic; (4) they are capable of sequencing or identifying markers in relatively long strands including strands of more than 100 bases; and (5) they are relatively economical and easy to use.

SUMMARY OF THE DRAWINGS

The above noted and other features of the invention will be better understood from the following detailed description when considered with reference to the accompanying drawings in which.

DETAILED DESCRIPTION

Figure 1:
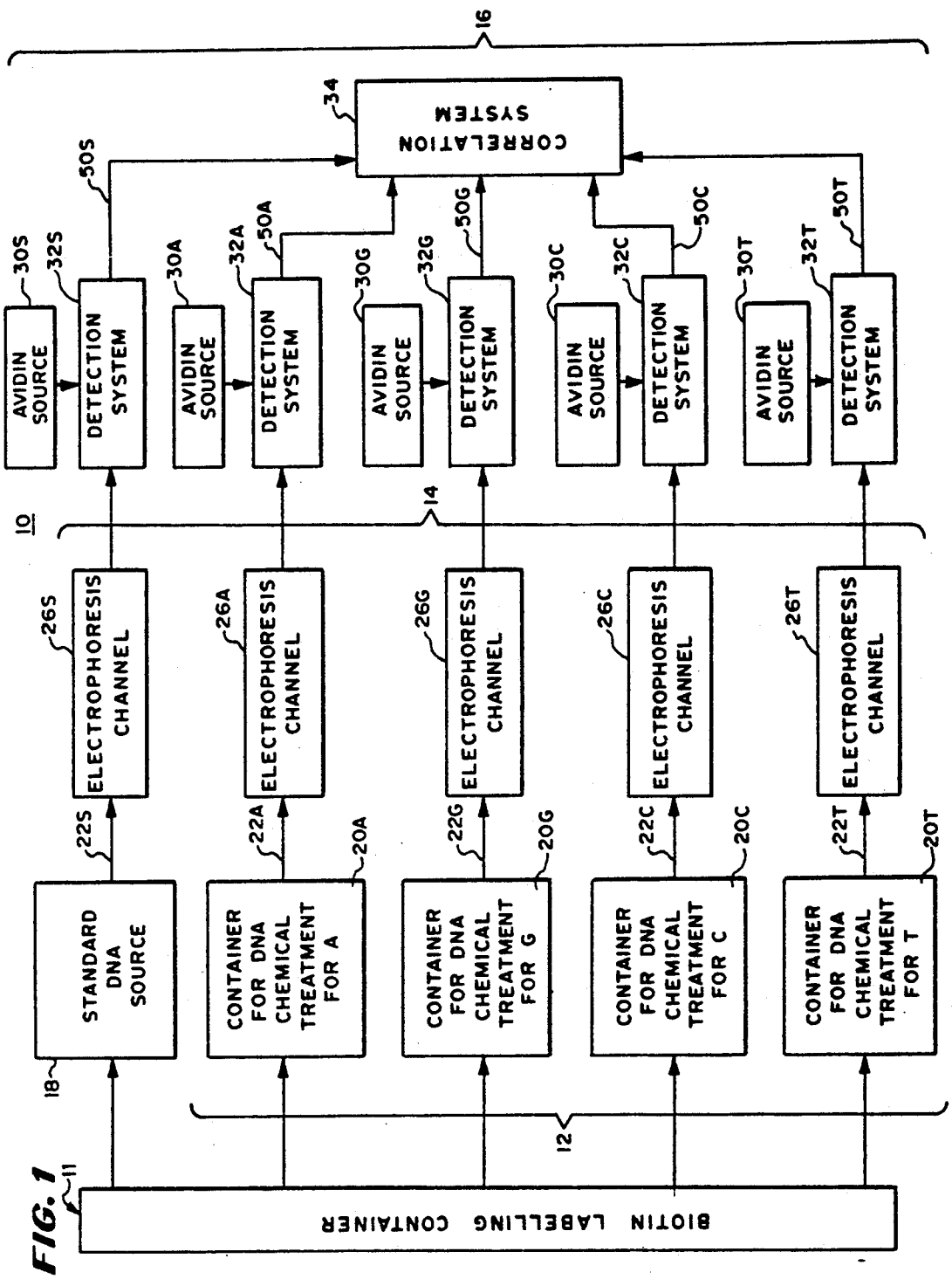
FIG. 1 is a block diagram of an embodiment of the invention.

In FIG. 1, there is shown a block diagram of one embodiment of a DNA sequencing system 10 having a biotin labeling system 11, a DNA cleavage system 12, a separating system 14, a detection and processing system 16 and a source of standard length DNA 18. The biotin from any suitable commercial source is attached to the cloned strands of more than 100 bases in a container as indicated at 11. The biotin preparation must be sufficient to mark at least one end of a substantial proportion of the DNA fragments with the biotin in a manner known in the art.

Although biotin has been selected as one marker which may be combined later with a larger fluorescently marked molecule such as avidin, other markers may be used. Such markers may be fluorescent and therefore do not require the subsequent combination with a larger fluorescently marked molecule such as avidin. In addition, multiple fluorescent markers may be attached to the DNA fragments. They must be of such a size and have such chemical characteristics to not obscure the normal differences in the mobilities between the different fragments due to cleavages at different ones of the adenine, guanine, cytosine and thymine bases and be able to be easily detected.

The DNA cleavage system 12 communicates in four paths and the source of standard length DNA 18 communicates in one path within the separating system 14 to permit passage of DNA fragments and standard fragments thereto in separate paths. The separating system 14, which sequences strands by separation, communicates with the detection and processing system 16 which analyzes the fragments by comparison with each other and the standard from the source of standard length DNA 18 to derive information about the DNA sequence of the original fragments.

The DNA cleavage system 12 includes four sources 20A, 20G, 20C and 20T of fragments of the same cloned DNA strand. This DNA strand is normally greater than 100 bases in length and is then further cleaved by chemical treatment to provide different lengths of fragments in each of four containers 20A, 20G, 20C and 20T.

In one embodiment, the container 20A contains fragments of DNA strands randomly cleaved by a chemical treatment for A, the container 20G contains fragments of DNA strands randomly cleaved by a chemical treatment for G; container 20C contains fragments of DNA strands randomly cleaved by a chemical treatment for C; and container 20T contains fragments of DNA strands randomly cleaved by a chemical treatment for T. Thus, identical fragments in each container have been cleaved at different bases of a given base type by the appropriate chemical treatment.

The fragments in the containers are respectively referred to as A-DNA fragments, G-DNA fragments, C-DNA fragments and T-DNA fragments from the containers 20A, 20G, 20C and 20T, respectively. These fragments are flowed from the containers 20A, 20G, 20C and 20T through corresponding ones of the conduits 22A, 22G, 22C and 22T into contact with the separating system 14. In the preferred embodiment, conduits 22A, 22G, 22C and 22T represent the pipetting of samples from containers 20A, 20G, 20C and 20T into the separately system 14.

The source of standard length DNA 18 includes a source of reference DNA fragments of known but different lengths which are flowed through a conduit 22S, such conduit including, but not limited to a pipetting operation to the separating system 14. These reference fragments have known lengths and therefore their time of movement through the separating system 14 forms a clock source or timing source as explained hereinafter. The cloned strands of 100 bases may be marked with biotin or with one or more fluorescent molecules before being divided into four batches or they may be marked instead after dividing into four batches, but before the selected chemical treatment.

The separating system 14 includes five electrophoresis channels 26S, 26A, 26G, 26C and 26T. The electrophoresis channels 26S, 26A, 26G, 26C and 26T include in the preferred embodiment, gel electrophoresis apparatus with each path length of gel being identical and having the same field applied across it to move samples continuously through five channels. The gels and fields are selected to provide a mobility to DNA strands that does not differ from channel to channel by more than 5% in velocity. In addition, the field may be varied over time to enhance the speed of larger molecules after smaller molecules have been detected, as well as to adjust the velocities in each channel based on feedback from the clock channel to compensate for differences in each channel such that the mobilities in each channel are within the accuracy required to maintain synchronism among the channels.

Preferably the gels are of the same materials, chemical derivatives and lengths and the electric fields are within 5% of the intermediates of each other in each channel. However, more than one reference channel can be used such that a reference channel is adjacent to a sample channel in order to minimize the requirements for uniformity of DNA movement in the gel for all channels.

The electrophoresis channel 26S receives fragments of known length DNA marked with biotin or with one or more fluorescent molecules and moves them through the gel. Similarly, each of the electrophoresis channels 26A, 26G, 26C and 26T receives labeled fragments from the cleavage system 12 and moves them in sequence through the sample electrophoresis channels, with each being moved in accordance with its mobility under a field identical to that of the reference electrophoresis channel 26S.

To provide information concerning the DNA sequence, the detection and processing system 16 includes five avidin sources 30S, 30A, 30G, 30C and 30T; five detection systems 32S, 32A, 32G, 32C and 32T and a correlation system 34. Each of the avidin sources 30S, 30A, 30G, 30C and 30T is connected to the detecting systems 32S, 32A, 32G, 32C and 32T. Each of the outputs from corresponding ones of the electrophoresis channels 26S, 26A, 26G, 26C and 26T within the separating system 14 is connected to a corresponding one of the detection systems 32S, 32A, 32G, 32C and 32T.

In the detection system, avid in with fluorescent markers attached and DNA fragments are combined to provide avidin marked DNA fragments with fluorescent markers attached to the avidin to a sample volume within the detection system for the detection of bands indicating the presence or absence of the fragments, which over time relates to their length. In the embodiment where the DNA strands are marked with one or more fluorescent markers rather than with biotin, it is not necessary to combine such DNA strands with avidin, and the DNA strands are moved directly into the detection system.

The output from each of the detection systems 32S, 32A, 32G, 32C and 32T are electrically connected through conductors to the correlation system 34 which may be a microprocessor system for correlating the information from each of the detection systems to provide information concerning the DNA sequence.

The avidin sources 30S, 30A, 30G, 30C and 30T each contain avidin purchased from known suppliers, with each avidin molecule in the preferred embodiment combined with three fluorescein molecules. The avidin sources are arranged to contact the DNA fragments and may be combined with the biotin-labelled DNA strands after such strands have been electrophoresed onto a moving blotting membrane.

The detection systems each include an optical system for detecting the presence or absence of bands and converting the detection of them to electrical signals which are applied electrically to the correlation system 34 indicating the sequence of the fragments with respect to both the standard fragments from the source of standard length DNA 18 and the A, G, C and T fragments from the containers 20A, 20G, 20C and 20T, respectively.

Figure 2:
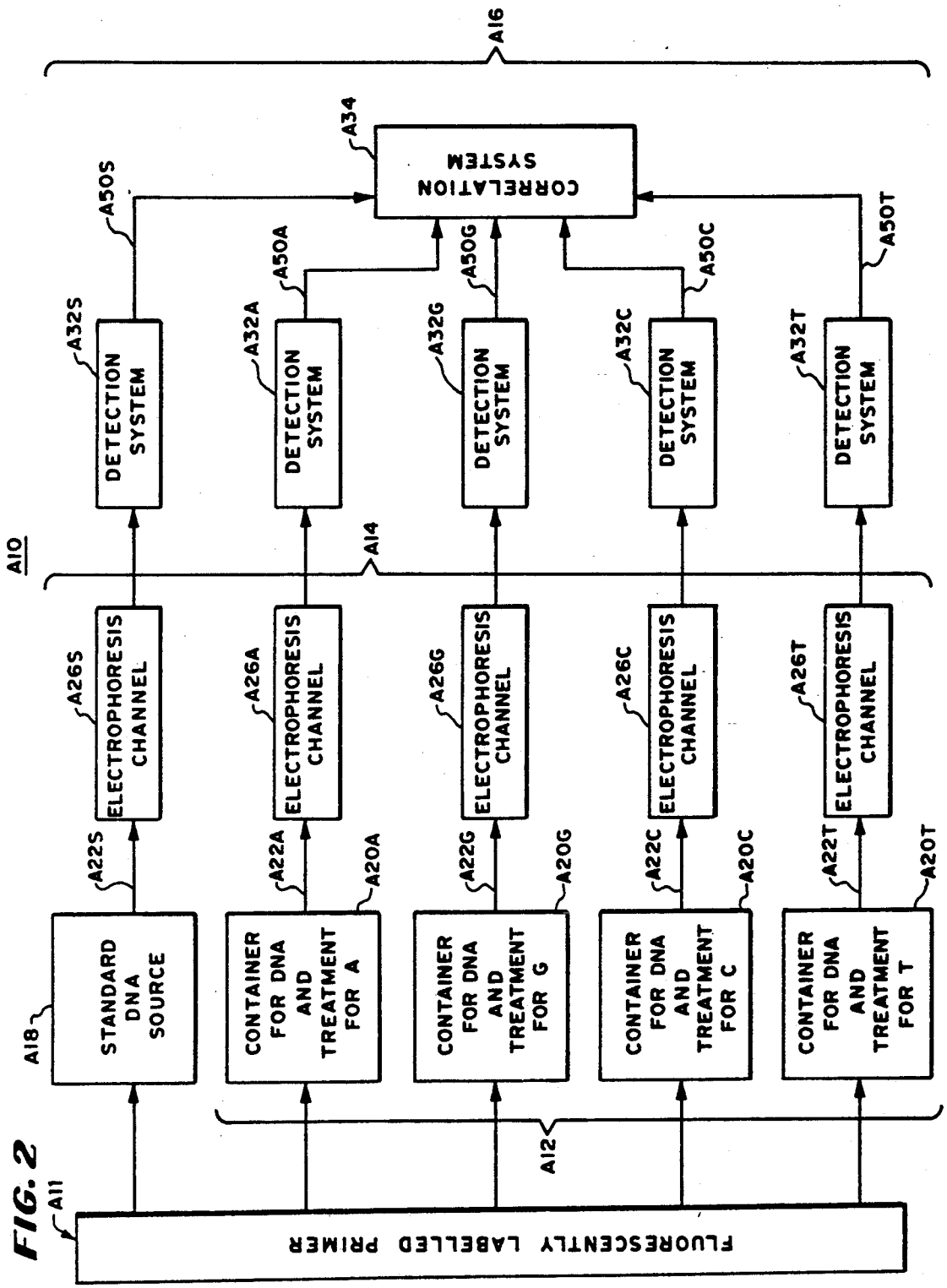
FIG. 2 is a block diagram of another embodiment of the invention.

In FIG. 2, there is shown a simplified block diagram of another embodiment of DNA sequencing apparatus A10. This apparatus is similar to the DNA sequencing apparatus 10 of FIG. 1 and the components are identified in a similar manner with the reference numbers being prefixed by the letter A.

In this embodiment, instead of the containers for DNA and chemical treatment for A, G, C and T of the embodiment of DNA sequencing system 10 shown at 20A, 20G, 20C and 20T in FIG. 1, the DNA sequencing apparatus A10 includes containers for treatment of the DNA in accordance with the method of Sanger described by F. Sanger, S. Nicklen and A. R. Coulson, "DNA Sequencing with Chain-Terminating Inhibiters", *Proceedings of the National Academy of Science, USA*, Vol. 74, No. 12, 5463–5467, 1977, indicated in the embodiment A10 of FIG. 2 at A20A, A20G, A20C and A20T shown as a group generally at A12.

In this method, the strands are separated and used as templates to synthesize DNA with synthesis terminating at given base types A, G, C or T in a random manner so as to obtain a plurality of different molecular weight strands. The limited synthesis is obtained by using nucleotides which terminate synthesis and is performed in separate containers, one of which has the special A nucleotide, another the special G nucleotide, another the special C nucleotide and another the special T nucleotide. These special nucleotides may be dideoxy nucleotides or marked nucleotides, both of which would terminate synthesis. Such marked nucleotides may be fluorescent. Each of the four batches will be terminated at a different one of the types of bases A, G, C and T randomly. This synthesis takes place in containers A20A, A20G, A20C and A20T.

In the preferred embodiment of FIG. 2, the template fragments are hybridized with a DNA primer having one or more fluorescent markers attached to it as shown at A11 before being applied to the channels indicated at A12 in FIG. 2. The design of fluorescently-labelled primers takes advantage of the process of designing small DNA fragments known as oligonucleotides. This process is described in the scientific and patent literature, such as for example U.S. Pat. No. 4,415,732, the disclosure of which is incorporated herein.

The synthesized strands, labelled by the fluorescently-marked primers, are electrophoresced in channels A26A, A26G, A26C and A26T. After the electrophoresis, the synthesized DNA fragments with the attached fluorescently-labelled primer are detected by the detection system using a wavelength of light appropriate to the emission spectrum of the fluorescent markers.

Figure 3:
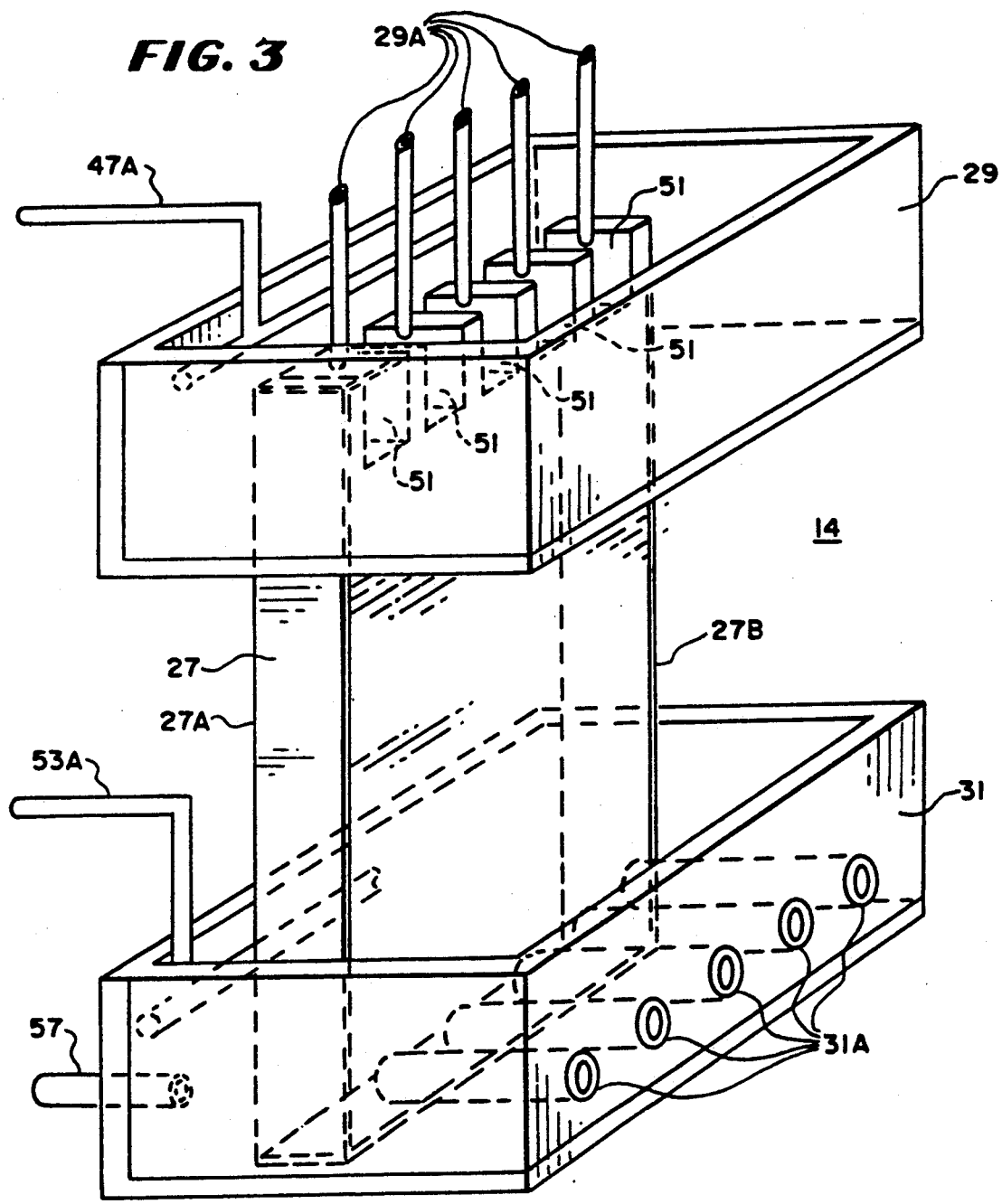
FIG. 3 is a simplified perspective view of a portion of the embodiment of FIGS. 1 and 2.

In FIG. 3, there is shown a separating system 14 which includes a slab of gel 27 as known in the art with five sample dispensing tubes indicated generally at 29A terminating in aligned slots 51 in the gel 27 on one end, with such slots in contact with a negative potential buffer well 29 having a negative electrode 47A, and five exit tubes at the other end located at 31A terminating in apertures in the gel 27, as well as a positive potential buffer well 31 having a positive electrode 53A.

The material to be electrophoresed is inserted into dispensing tubes 29A and due to the field across the gel 27 moves from top to bottom in the gel and into the appropriate corresponding exit tubes of the group 31A. The gel slab 27 has glass plates 27A and 27B on either side to confine the sample and gel. Buffer fluid from the buffer well 31 is pumped at right angles to the gel 27 from a source at 57 by pumps connected to exit tubes 31A to pull fluid there through. The buffer fluid picks up any DNA that is electrophoresed into the exit tubes 31A and makes its way to sensing equipment to be described hereinafter or to provide communication with other gel slabs for futher electrophoresis of the DNA strands being electrophoresed from the slab 27.

Figure 4:
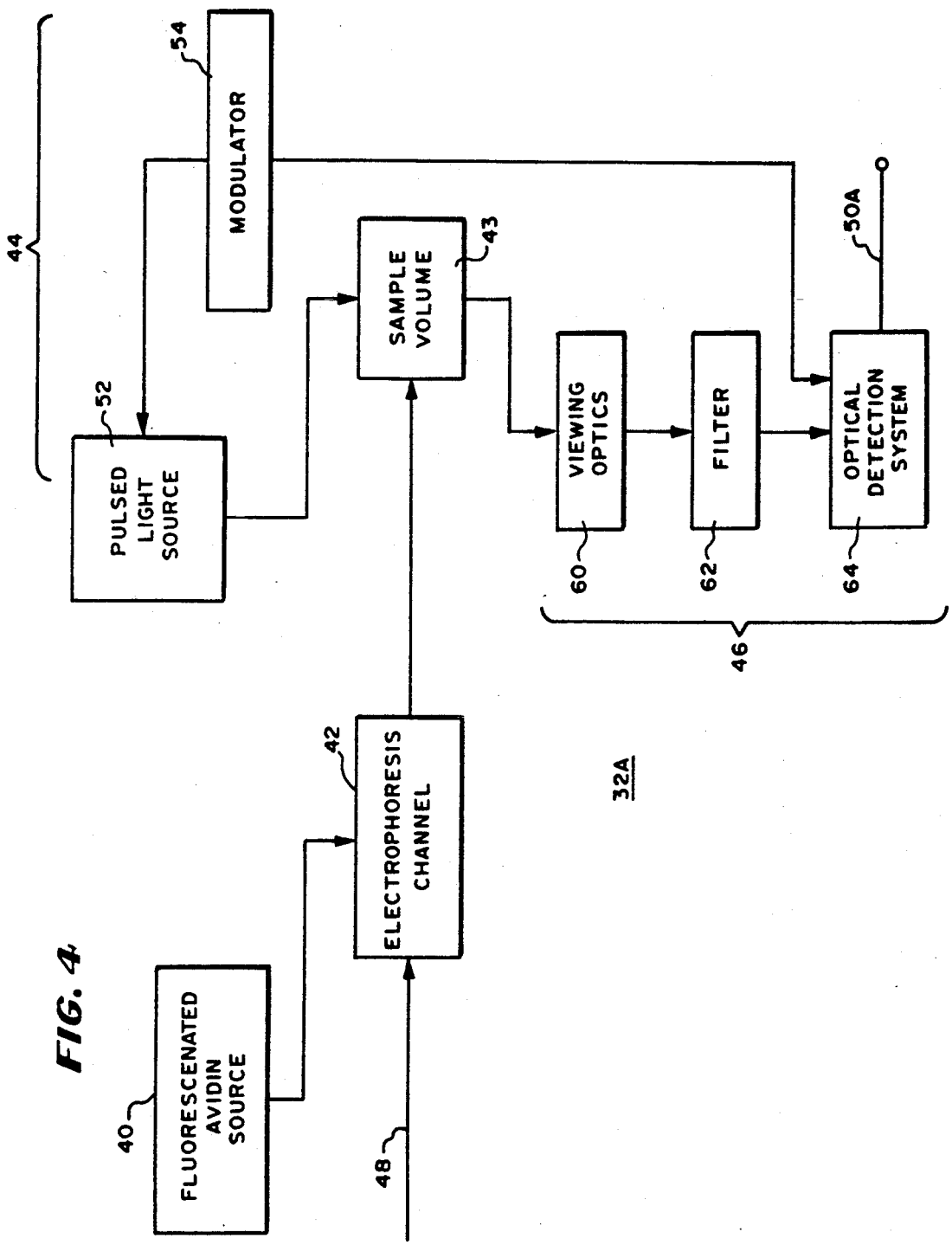
FIG. 4 is a block diagram of a portion of the embodiment of FIGS. 1 and 2.

In FIG. 4, there is shown a block diagram of the detection system 32A. The detection systems 32S, 32G, 32C and 32T (not shown in FIG. 4) are substantially identical to the detection system 32A and so only the system 32A will be described in detail herein. The detection system 32A includes an electrophoresis channel 42 (which may be a continuation of electrophoresis channel 26A as indicated in FIG. 1), a sample volume 43 (which may be part of electrophoresis channel 42), a light source 44 and an optical detection system 46.

In one embodiment, avidin marked with fluorescein in fluorescenated-avidin source 40 is brought into contact with the gel which receives A type terminated strands from electrophoresis channel 26A (FIG. 1) on conduit 48 and such fluorescein-labelled avidin is attached to the biotin-labelled DNA fragments. The electrophoresis channel 42 may be a continuation of electrophoresis channel 26A for continuous electrophoresing. After the fluorescein-labelled avidin is attached to the biotin-labelled DNA in the electrophoresis channel 42, the complex molecule is moved into the sample volume 43.

The sample volume 43 is irradiated by the light source 44. Light from the light source 44 is detected and converted to electrical signals by the optical detection system 46 for application through a conductor 50A to the correlation system 34 (FIG. 1). In one embodiment, the fluorescenated-avidin source 40 contains a fluorescent marker having a period of fluorescence sufficiently long compared to background fluorescence of the gel and associated materials to permit significant separation of the signal from the fluorescence.

The light source 44 includes a pulsed light source 52 and a modulator 54. The pulsed light source 52 is selected to emit light within the absorbance spectrum of the fluorescent marker. In one embodiment, the modulator 54 controls the pulsed light source 52 to select intervals between pulses, the intervals being provided to permit the decay of fluorescent light from the background fluorescent material, during which time the fluorescent light from the fluorescent markers is measured.

These time periods between pulses are sufficiently long to emcompass the entire delay period. This is done because the delay period of the attached fluorescent marker is relatively long compared to background noise fluorescence and so a period of time may pass before the measurement is made by the optical detection system 46. Typically, the pulse of light has a duration of approximately three nanoseconds and the background fluorescence decay lasts for approximately ten nanoseconds while the fluorescent marker has a decay lifetime of 100 nanoseconds.

Typically, the optical detection system 46 begins reading at approximately 50 nanoseconds after the initiation of the excitation pulse from a laser and continues for approximately 150 nanoseconds until 200 nanoseconds after the initiation of the three nanosecond pulse. Although in this embodiment, a pulsed laser light source 52 is utilized, a broad bandlight source combined with filters or a monochrometer may be utilized to provide the narrow band in the absorption spectrum of the marker.

Another embodiment uses an electro-optic modulator which modulates a continuous light source at a frequency typically at 10 khz, with essentially 100% depth of modulation and 50% duty cycle. A pulse generator provides a signal both to the modulator through a driver and to a lock-in amplifier as a reference signal. Another embodiment provides modulation of a laser diode light source through the pulsing of the drive current to the laser diode. Modulation may typically be at frequencies between 100 and 15,000 hz with a 50% duty cycle. A lock-in amplifier is used to synchronously demodulate the fluorescent signal. Another embodiment uses a spinning chopping wheel to modulate a continuous light source. Because the background fluorescence signal from glass (soda lime, borosilicate, quartz, etc.) has a larger time constant than that of the fluorescent marker; temperal discrimination is accomplished by modulating the light source. Still another embodiment uses a continuous light source with no modulation.

To detect the bands in the electrophoresis gel of the electrophoresis channel 42 indicating particular DNA fragments, the optical detection system 46 includes certain viewing optics 60, a filter 62, and an optical detection system 64. The filter 62 selects the wavelength of light transmitted through it by the viewing optics 60 which focuses the light onto the optical detection system 64. The optical detection system 64 is electrically connected to the modulator 54. The signal on conductor 50A indicates the presence or absence of a band of DNA fragments in the sample volume 43.

The filter 62 in this embodiment includes an interference filter having a pass band corresponding to the high emission spectrum of the fluorescent marker. Such filters are known in the art and may be purchased from commercial sources with bands to correspond to common emission bands of fluorescent markers. In addition, there may be long-wavelength-passing intereference filters and/or colored glass filters. Another embodiment uses a monochrometer instead of a filter.

The viewing optics 60 consists of a lens system positioned in juxtaposition with filter 62 to focus light onto the optical detection system 64. It may be any conventional optical system, and the optical detection system 64 should include a semiconductor detector or a photomultiplier tube, such as the Model R928 made by Hamamatsu, Japan.

In the first embodiment, the output of the photomultiplier or semiconductor detector is gated in response to the signals from the modulator 54 to occur after a time delay after each pulse from the pulsed laser light source 52. For example, a time delay may be included before the electrical signal is applied to an amplifier and thus provide an electrical signal to the conductor 50A or to an amplifier, the output of which is electrically connected to the conductor 50A. In the preferred embodiment, the time delay is 50 microseconds and the gate or amplifier is maintained opened by a monostable multivibrator for approximately 150 nanosecons. In a second embodiment, the square wave output of a modulator is used as a reference for the signal from the detector, with a lock-in amplifier providing synchronous demodulation. In a third embodiment, no modulation is performed.

Figure 5:
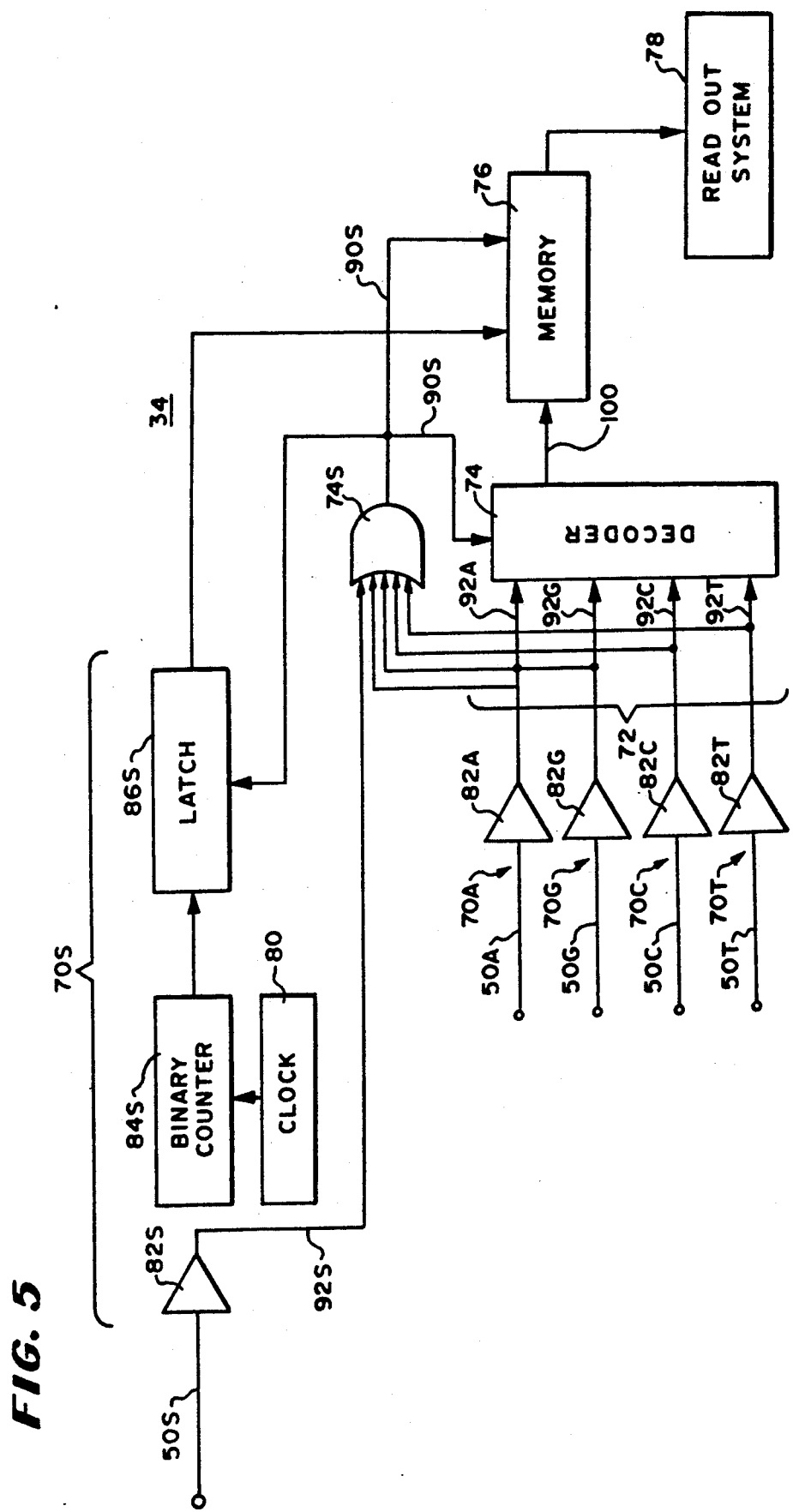
FIG. 5 is a schematic circuit diagram of a protion of the embodiment of FIGS. 1 and 2.

In FIG. 5, there is shown a block diagram of the correlation system 34 having a standard channel input circuit 70S, a gating system 72, a decoder 74, a memory 76 and a read-out system 78. An OR gate 74S is electrically connected to: (1) the standard channel input circuit 70S; (2) other channels 70A, 70G, 70C and 70T; and (3) the gating system 72. The gating system 72 receives channel input signals from each of the channels 70A, 70G, 70C, and 70T similar to that of channel 70S.

The OR gate 74S is electrically connected to the memory 76 which receives signals from decoder 74 indicating the presence of DNA fragments in the particular one of the nucleic acid bases or in the standard channel. The memory 76 is electrically connected to the read-out system 78 to print out the sequence.

The standard channel input circuit 70S includes a pulse shaper 82S, a binary counter 84S, and a latch 86S, with the input of the pulse shaper 82S being electrically connected to a conductor 50S and its output being connected to OR gate 74S. The output of the binary counter 84S is connected to the latch 86S to provide a time increment signal to the latch 86S, the output of which is applied to one of the inputs of memory 76 when triggered by a signal from OR gate 74S. The conductor 50S corresponds to conductors 50A, 50H, 50C and 50T except that conductor 50S is the output for the standard clock channel rather than for adenine, guanine, cytosine or thymine.

The latch 86S and the decoder 74 are pulsed by a signal from the OR gate 74S to write into the memory 76 for recording with a distinctive signal indicating a clock timing pulse which is later printed to indicate the time that particular DNA segments have been received and detected in the detection system 32A, 32G, 32C and 32T (FIG. 1). The binary counter 84S receives clock pulses from clock 80 to which it is connected and thus contains a binary signal representing time for application to the latch 86S.

The gating system 72 includes a decoder 74 which is electrically connected to four inputs from channels 70A, 70G, 70C and 70T respectively, for receiving signals indicating the presence of types A, G, C, and T fragments as they appear on input conductors 50A, 50G, 50C and 50T. The signals on conductors 50A, 50G, 50C and 50T are each applied to respective ones of the pulse shapers 82A, 82G, 82C and 82T, the outputs of which are electrically connected through corresponding ones of the conductors 92A, 92G, 92C, and 92T to different inputs of the decoder 74 and to inputs of the OR gate 74S, so that the decoder 74 receives signals indicating the presence of a DNA fragment for application to the memory 76 upon receiving a signal on conductor 90S from the OR gate 74S. The OR gate 74S applies such a signal when receiving a signal from any one of the channels 70S, 70A, 70G, 70C, and 70T, so that the memory 76 receives clock timing signals and signals indicating DNA for reading to the readout system 78. The output of the decoder 74 is electrically connected to the memory 76 through a conductor 100.

Figure 6:
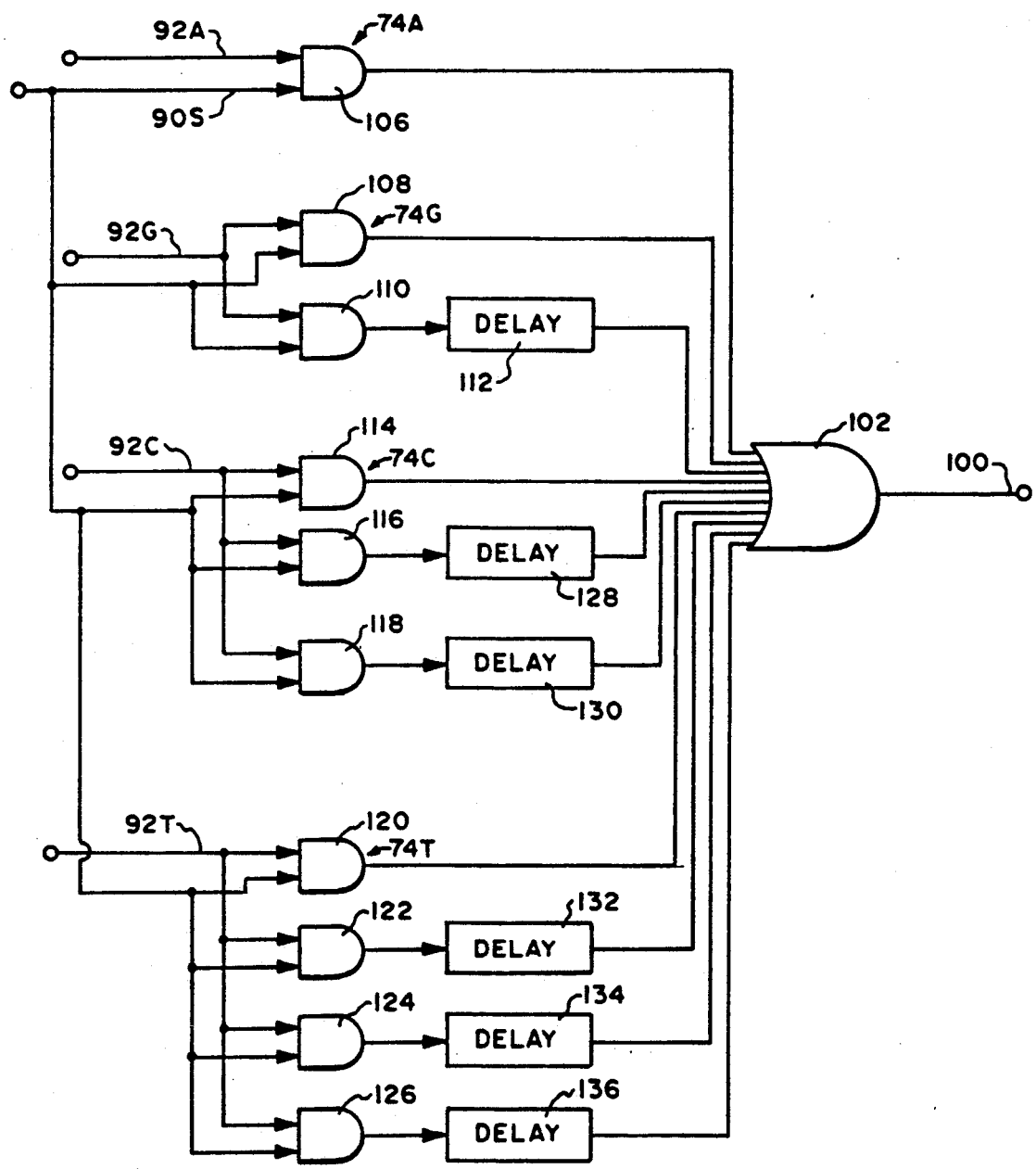
FIG. 6 is a schematic circuit diagram of a portion of the schematic diagram of FIG. 5.

In FIG. 6, there is shown a schematic circuit diagram of the decoder 74 having an OR gate 102 and a plurality of coding channels 74A, 74G, 74C and 74T to respectively indicate fragments terminating with the bases, adenine, guanine, cytosine and thymine respectively.

The coding channel 74A includes AND gate 106, having its inputs electrically connected to conductor 92A and 90S to receive on conductor 90S a clock signal from the OR gate 74S (FIG. 5) and on its other input a signal indicating the presence of an adenine terminated fragment on conductor 92A.

Channel 74G includes AND gate 108, AND gate 110 and delay line 112. Conductor 92G indicating a guanine terminated strand is electrically connected to the inputs of AND gate 108 and 110. The output of AND gate 108 is connected to one of the inputs of OR gate 102 and the output of AND gate 110 is electrically connected through delay line 112 to the input of OR gate 102 to provide two pulses in succession to OR gate 102. Thus, channel 74A applies one out pulse from the output of AND gate 106 to one of the inputs of OR gate 102, whereas channel 74G applies two pulses. In either case, the sequence of pulses indicates the presence of a particular one of the types of DNA fragments A or G.

Similarly, the channel 74C includes AND gates 114, 116 and 118, each having one of its two inputs electrically connected to conductor 92C and 90S and the channel 74T includes AND gates 120, 122, 124 and 126, each having one of its inputs electrically connected to conductor 92T and the other connected to conductor 90S. The output from AND gate 114 is electrically connected to an input of OR gate 102, the output of AND gate 116 is electrically connected through a delay 128 to the input of OR gate 102, and the output of AND gate 118 is electrically connected through a delay 130 longer than the delay 128 to an input of the OR gate 102. With this arrangement, the presence of a DNA strand terminating with cytosine results in three pulses to the OR gate 102.

The output of AND gate 120 is electrically connected to an input of the OR gate 102, the output of the AND gate 122 is electrically connected through a delay 132 to an input of the OR gate 102, the output of AND gate 124 is electrically connected through a delay 134 longer than the delay 132 to an input of the OR gate 102 and the output of AND gate 126 is electrically connected through a delay 136 longer than the delay 134 to an input of the OR gate 102. In this manner, the presence of a thymine-terminated fragment results in four signals in series to the inputs of OR gate 102. The output terminal of OR gate 102 is applied to the output conductor 100 so as to provide a coded signal indicating the presence of a particular DNA group to the memory 76 (FIG. 5) coordinated with a clock timing signal.

Figure 7:
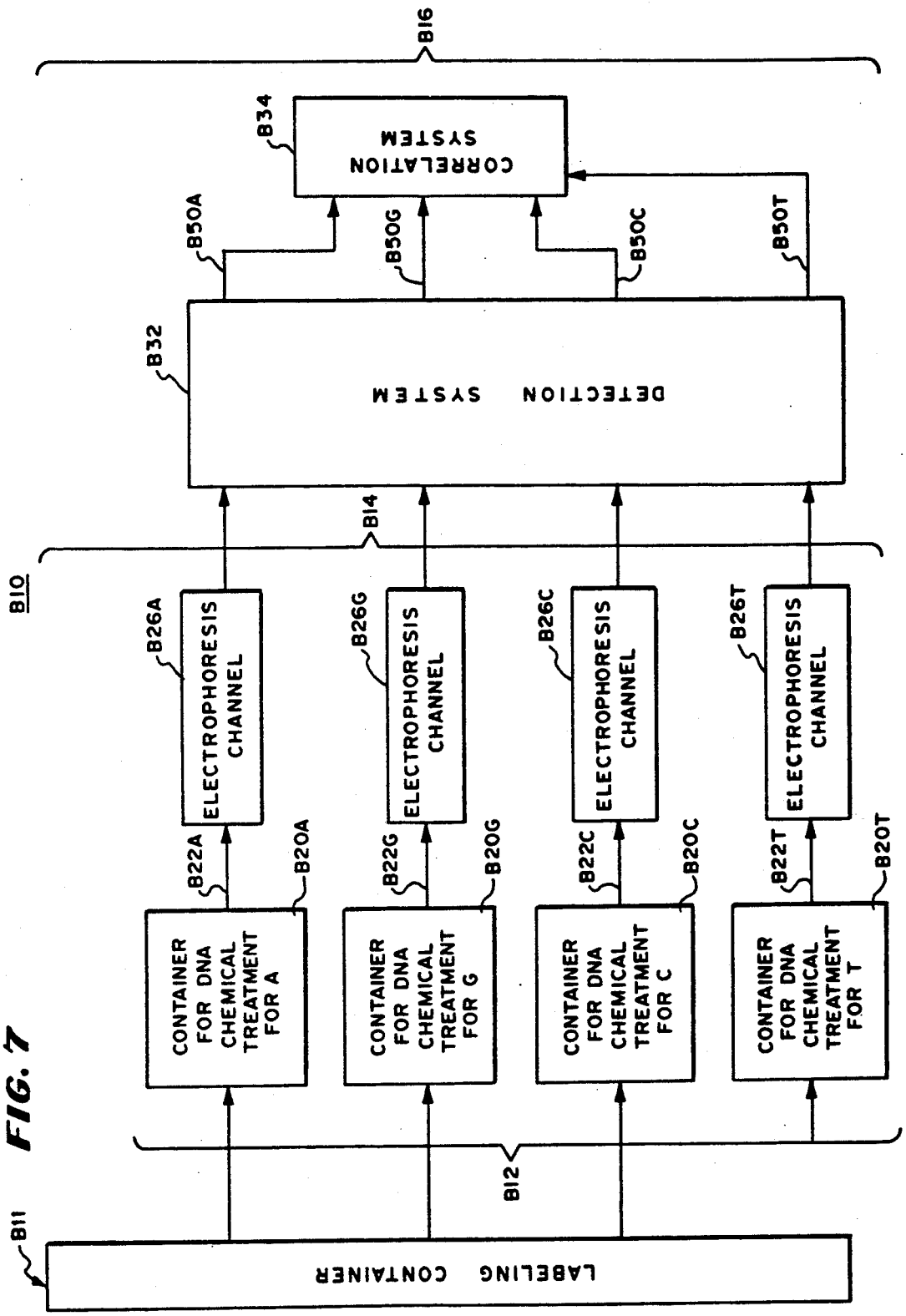
FIG. 7 is a block diagram of still another embodiment of the invention.

In FIG. 7, there is shown a simplified block diagram of another embodiment of DNA sequencing apparatus B10. This apparatus is similar to the DNA sequencing apparatus 10 of FIG. 1 and the components are identified in a similar manner with the reference numbers being prefixed by the letter B. However, the strands of DNA are labeled in labeling container B11 with one or more fluorescent molecules. Containers for treatment of the strands to form fragments to A, G, C or T terminations in different containers are indicated in the embodiments B10 of FIG. 7 at B20A, B20G, B20C and B20T shown as a group generally at B12.

In this method, single-stranded DNA are marked with fluorescent dye. In one such method, the single-stranded DNA are separated into four aliquots at B11, which are used as templates to synthesize DNA with synthesis terminating at given base types A, G, C or T in a random manner to obtain a plurality of different molecular weight strands. The limited synthesis is obtained by using nucleotides which will terminate synthesis and is performed in separate containers, one of which has the special A nucleotide, another the special G nucleotide, another the special C nucleotide and another the special T nucleotide. These special nucleotides may be dideoxy nucleotides or other nucleotides, including marked nucleotides, which terminate synthesis, so that each of the four batches are randomly terminated at a different one of the types of bases A, G, C and T. If the nucleotides are marked, such marking may be with fluorescent markers. After being separated by electrophoresis, the bands are detected by light.

To mark DNA fragments, the template DNA strands are hybridized with a DNA priming oligonucleotide which has a fluorescent marker attached to it. The marker primer is elongated randomly to a selected base type. In another embodiment, the priming DNA oligonucleotide is unmarked, but synthesis is terminated with a fluorescently marked special nucleotide. In either case, the strands are marked. In the preferred embodiment, they are marked with a infrared fluorescent molecule.

To separate the fragments, the marked fragments are each individually electrophoresced through gel in different channels or in different columns. The gel and the field must be uniform although the optional use of one or more reference channels reduces uniformity requirements. When a single slab is used to migrate several different samples, the channels must be kept separate but should be sufficiently close to one another so that the voltage gradient and temperature are uniform for each channel. Preferably, the pH of the gel for separation is 7-10.

The DNA fragments separate in accordance with their length during electrophoresis. Thus, the fastest migrating fraction is the fragment which is synthesized to the first base closest to the priming DNA oligonucleotide and since the channels are separate, it is known which base A, G, C or T is the first one in the sequence from the channel.

The next band in time in the gel is the molecule or molecules which is one base longer than the first one since it encompasses both the first base and the second one from priming DNA oligonucleotide. Similarly, the third fragment to form a band during electrophoresis encompasses the first three base units and so on.

Because a large number of bases are to be sequenced, there is a large number of bands of DNA strands and the number of strands in each band is relatively low. Thus, the gel and the voltage field must be selected to provide adequate separation for detection. The gel slab is sufficiently long such that the more mobile bands near the end of the gel are fully resolved while the less mobile bands near the entrance end of the gel are unresolved in a continuous process. More specifically, at least 10 percent of the bands have been resolved by electrophoresis in the gel while the less mobile bands which are near the entrance end of the gel are not fully resolved.

In one embodiment, the bands are scanned by a light source that applies pulsed or chopped light at a repetition rate of 100–15,000 hz. The frequency of the light in the pulses is within the optimum absorption spectrum of the fluorescent marker. The light is sensed using a lock-in amplifier which uses sychronous demodulation to discriminate the fluorescent signal from the DNA strands against the background fluorescent signal, which has a longer time constant. The resulting electrical signal is amplified and correlated to provide the sequence of DNA.

Figure 8:
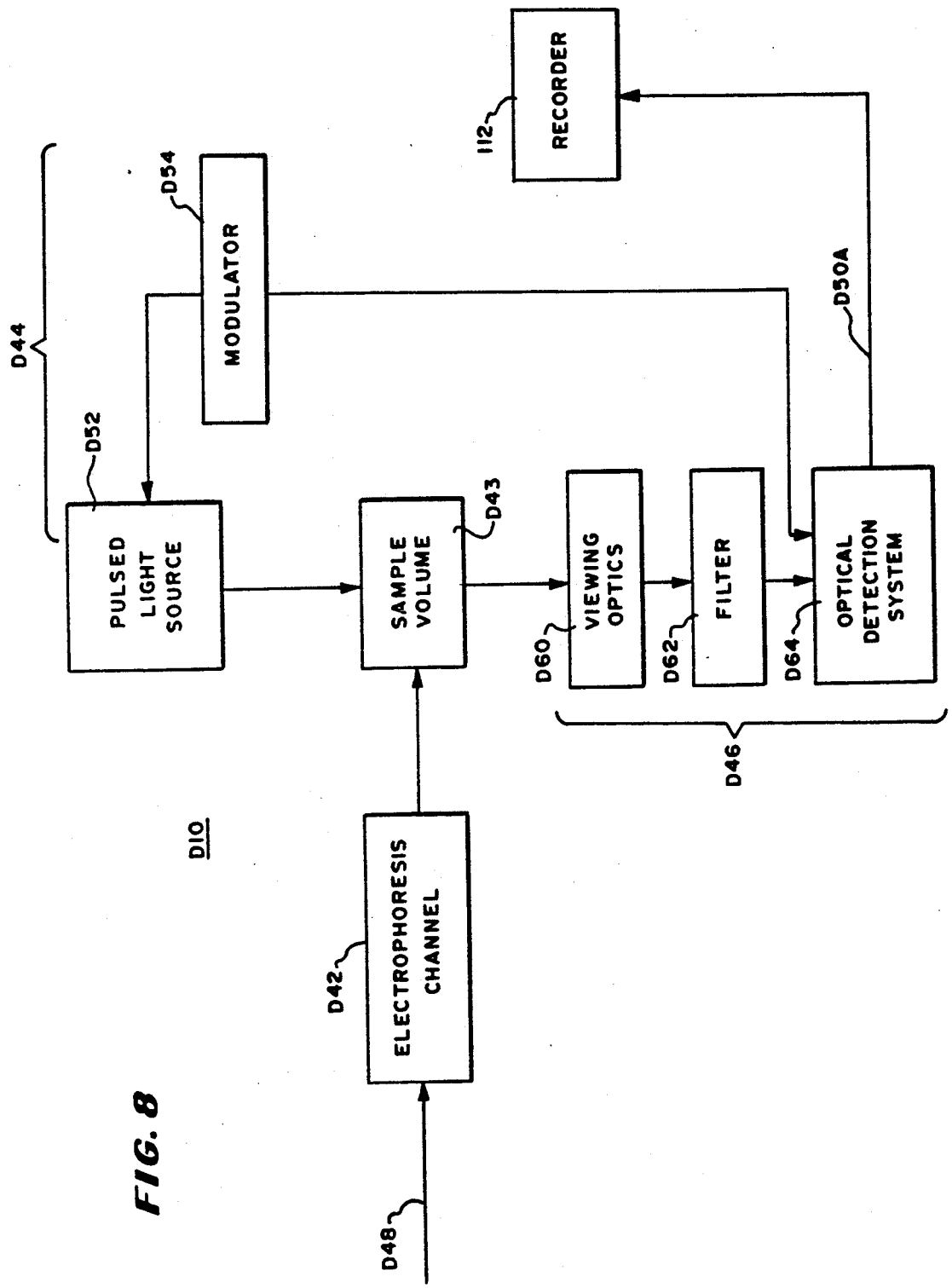
FIG. 8 is a block diagram of still another embodiment of the invention.

In FIG. 8, there is shown a block diagram of another embodiment D10 of the invention used for identifying band patterns of DNA strands prepared by such techniques as restriction enzyme cutting or polymerase chain reaction (PCR). The DNA strands are marked by direct labelling of fluorescent markers to the strands or by detecting fluorescently-labelled probes hybridized to the separated strands.

Cutting DNA strands with restriction enzymes and then electrophoresing such strands results in band patterns known as DNA restriction fragment length polymorphisms (RFLP). In restriction fragment length polymorphisms or in the diagnosis of DNA using polymerase chain reaction (PCR), a fingerprint or identification of a single type of DNA is obtained using two identifying components, which are: (1) restriction enzymes or PCR primers; and (2) marked probes.

The first component is utilized in a conventional manner to treat cellular DNA and produce the fragments near or within a gene of interest. The restriction enzymes cut only at specific nucleotide sequences, referred to as recognition sites. The PCR primers allow amplification of only those DNA strands having sequences complementary to such primers.

The second component is used to identify the inherited nucleotide patterns. To identify the inherited nucleotide patterns, which in some cases indicate a disease or other unique characteristic, patterns are obtained indicating the presence of fragments generated by restriction enzyme cutting or PCR amplification from a number of cells of a related group such as of a family. These patterns are compared. An abnormal pattern indicates an abnormal gene and may be identified when correlated with the pattern of other members having the same gene pattern in the group. Thus, a particular gene representing a disease or abnormality or other feature of interest such as characteristics of a particular strain of plant; or the presence of foreign genetic material; or the like is identified.

The basic steps of RFLP or of generating fragments by PCR are not by themselves part of the invention but only the method and apparatus described herein for expediting the obtaining of the patterns by enabling continuous processing in a manner similar to the other embodiments of this invention. In this process, the DNA fragments are either fluorescently labelled directly or hybridized with fluorescently labelled probes and then electrophoresed in the channel D42. The fragments are electrophoresed into the sample volume D43, which may, in actuality, be an extension of the gel, where they are detected as described in the embodiments of FIGS. 4 and 7. As they flow through the channels, the fragments are detected and an identifying indication recorded on the recorder 112. The recorder 112 may be a strip chart recorder, magnetic recorder or any other recorder which indicates the sequence of the fragments for comparison with other patterns against a time base from similar cells to provide an indication of differences.

Figure 9:
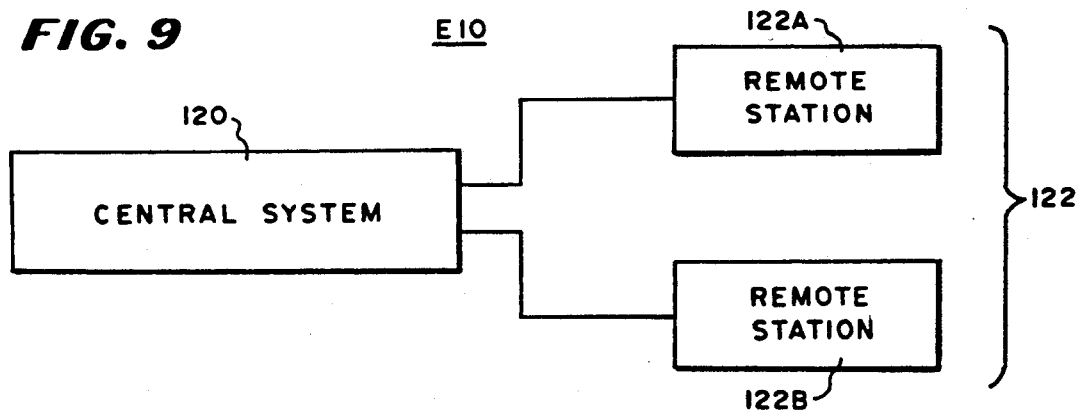
FIG. 9 is a block diagram of another embodiment of the invention.

In FIG. 9, there is shown another embodiment E10 of sequencing system having a central system 120 and a plurality of remote stations, two of which are shown at 122A and 122B. The remote stations 122A and 122B each are able to perform the sequencing but some portions of data processing can only be performed by the central station 120. It may supply data to the remote stations, such as 122A and 122B, to which it is electrically connected and receive data from them. With this arrangement, the central sequencing system 120 may cooperate with one or more of the remote stations, such as 122A and 122B, for increased capability such as increased number of channels. Each unit may control the parameters used in sequencing, such as the electrophoresis potential or the like.

Figure 10:
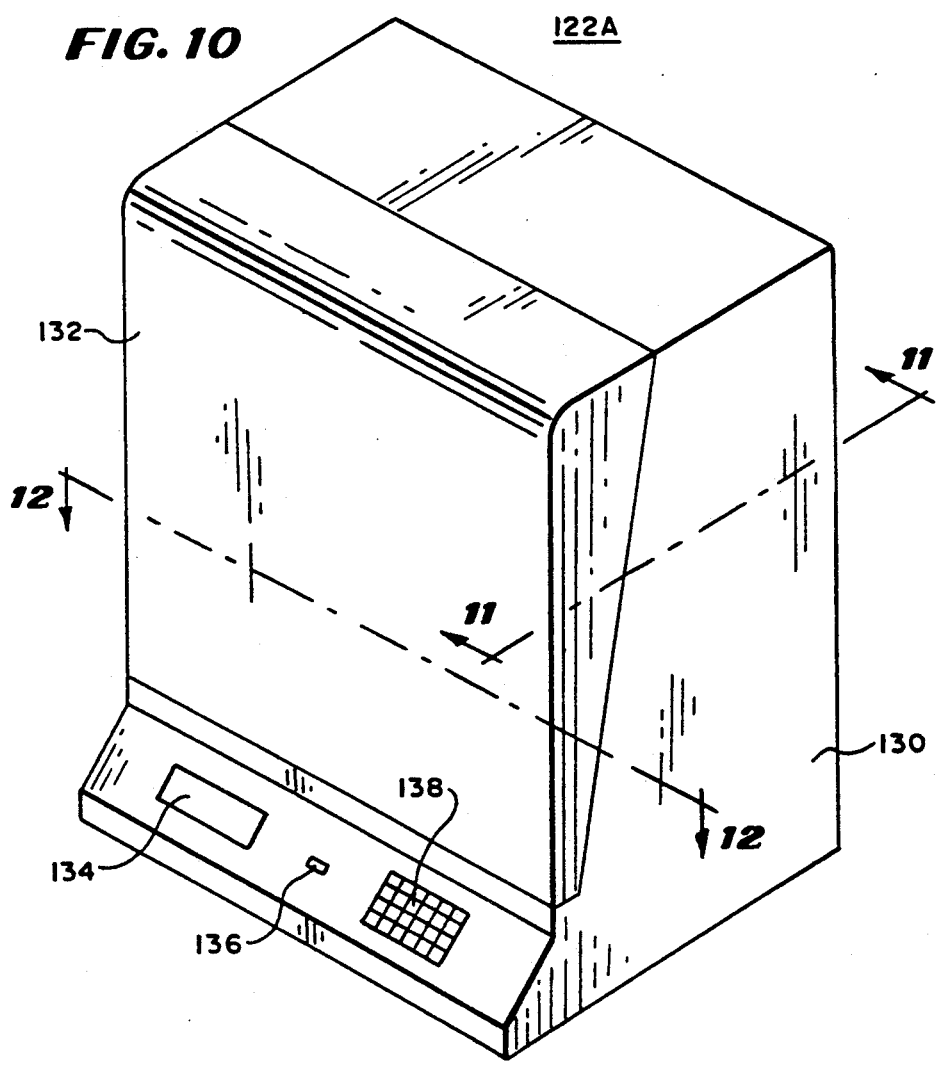
FIG. 10 is a perspective view of a portion of the embodiment of FIG. 9.

In FIG. 10, there is shown a simplified view of the remote station 122A having a cabinet housing 130, a front cover 132, a liquid crystal display readout 134, a high voltage warning light 136 and a plurality of function keys 138. In FIG. 10, the remote system 122A is shown closed. However, the front cover 132 may be removed to expose an electrophoresis section. The potential applied across the gel may be set and different data readouts may be selected either from the analysis provided within the central system 120 (FIG. 9) or values from within the remote station 122A using the function key pad 138 and the selected data displayed on the liquid crystal display readout 134 prior to and/or after selection.

Figure 11:
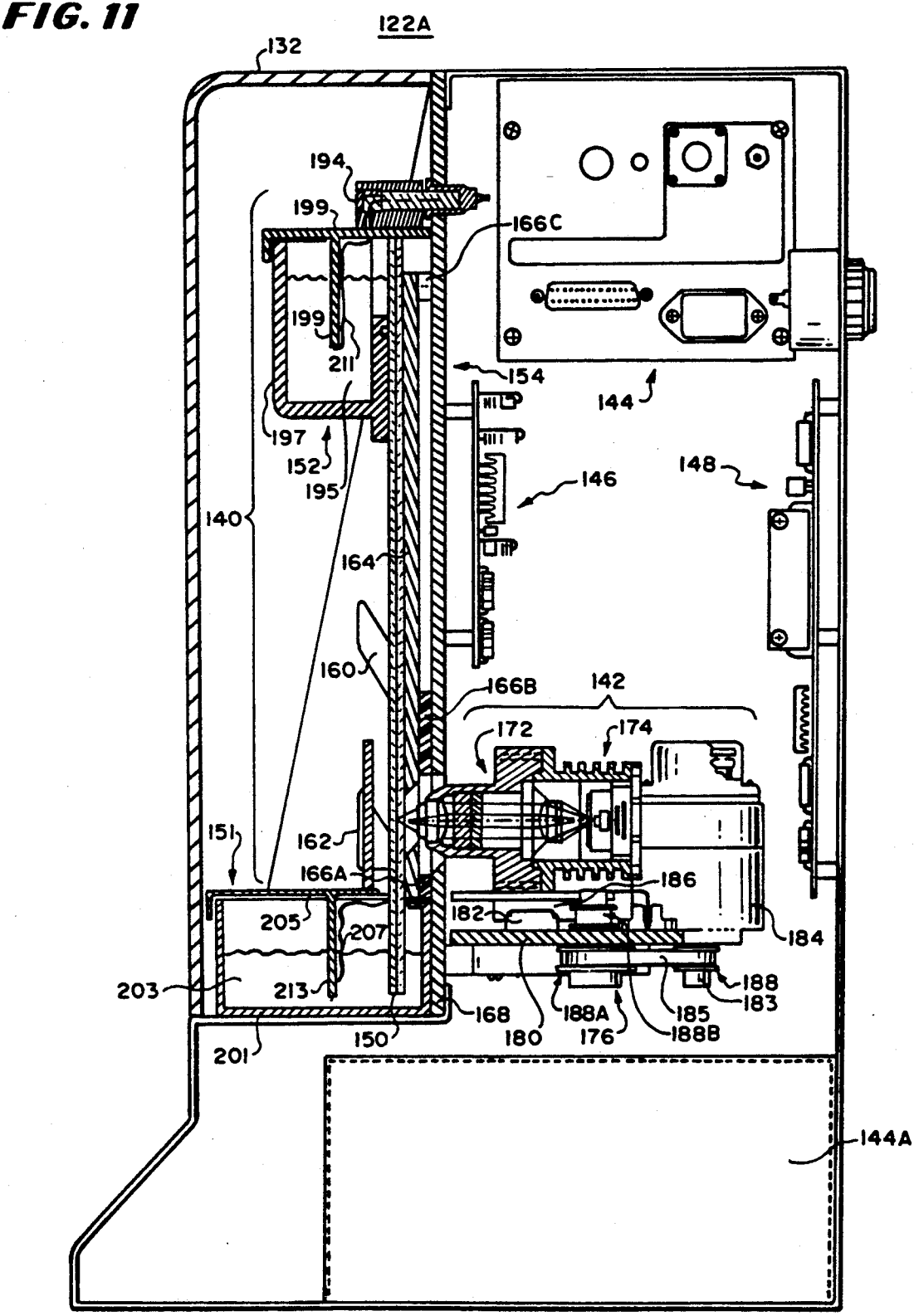
FIG. 11 is a sectional view taken through lines 11—11 of FIG. 10.

In FIG. 11, there is shown a sectional view of the remote station 122A taken through section lines 11—11 of FIG. 10 having an electrophoresis section 140, a scanning section 142, an electrophoresis power supply 144, a system power supply section 144A, an analog board 146 and a digital board 148. The electrophoresis section 140 is positioned near the front of the cabinet and a portion of it is adapted to be scanned by the scanning section 142 in cooperation with circuitry on the analog board 146 and the digital board 148. All of the apparatus are electrically connected to the power supply section 144A for such operation.

To separate different DNA fragments into bands, the electrophoresis section 140 includes a gel sandwich 150, an upper buffer assembly 152, support assembly 154, and a lower buffer assembly 151 positioned to enclose the bottom of the gel sandwich 150. In the embodiment of FIG. 11, the gel sandwich 150 is held substantially vertically and its temperature is controlled during operation. Bands are separated by applying voltage to the upper buffer assembly 152 and lower buffer assembly 151 and scanned by the scanning section 142.

To support the gel sandwich 150, the support assembly 154 includes a pair of upper side brackets and lower side brackets 160 and 162 (only one of each pair being shown in FIG. 11), a temperature control heating plate 164, and a plastic spacer, shown at 166A-166C, in FIG. 11. The entire structure is supported on the support assembly 154 which mounts the upper and lower side brackets 160 and 162.

The upper and lower side brackets 160 and 162 are shaped to receive the gel sandwich 150 and hold it in place in juxtaposition with the scanning section 142. The spacer as shown as 166A-166C space the temperature control heating plate 164 from an apparatus support plate 168 and maintain it at a constant selected temperature above ambient temperature. In the preferred embodiment, the temperature is maintained at 50 degrees Centigrade and should be maintained in a range of 30 degrees to 80 degrees.

The scanning section 142 includes a laser diode assembly (not shown in FIG. 11), a microscope assembly 172, a photodiode section 174 and a scanner mounting section 176. The laser diode assembly (not shown in FIG. 11) is positioned at an angle to an opening in the heating plate 164 so that light impinges on the gel sandwich 150 to cause fluorescence with minimum reflection back through the microscope assembly 172.

To receive the fluorescent light, the microscope assembly 172 is focused on the gel sandwich 150 and transmits fluorescent light emitted therefrom into the photodiode section 174 which converts it to electrical signals for transmission to and processing by the analog and digital boards 146 and 148 which may provide further analysis of data. The scanning section 142 moves along a slot in the apparatus support plate 168 which is mounted to the scanner mounting section 176 during this operation in order to scan across the columns in the gel sandwich 150.

The scanner mounting section 176 includes a mounting plate 180, a bearing 182, a stepping motor 184, a slidable support 186 and a belt and pully arrangement 185, 188, 188A. The mounting plate 180 is bolted to the apparatus support plate 168 and supports an elongated bearing plate 182, a stepping motor 184 and two pulleys 188 and 188A. The elongated bearing plate 182 extends the length of the gel sandwich 150.

To permit motion of the laser diode assembly (not shown) and microscope assembly 172 with respect to the gel sandwich 150, the slidable support 186 supports the microscope assembly 172 and diode assembly and slidably rests upon the bearing plate 182. An output shaft 183 of the stepping motor 184 drives a pulley 188B through pulley 188, belt 185, and pulley 188A and the pulley 188B drives a belt (not shown) that is clamped to the slidable support 186 to move it the length of the gel sandwich 150 during scanning by the laser diode and microscope assembly 172 which rest upon it. The stepping motor 184 under the control of circuitry in the digital board 148 moves the pulley 188B to move the belt (not shown) and thus cause scanning across the gel sandwich 150.

As shown in this view, the electrophoresis power supply 144 is electrically connected to buffer in the upper buffer assembly 152 through an electrical connector 194 and to the lower buffer assembly 151 through a connector not shown in FIG. 11.

The upper buffer assembly 152 includes walls 197 forming a container to hold a buffer solution 195 and a cover 199 formed with a lip to fit over the walls 197 from the top and containing a downwardly extending flat member spaced away from the side walls and holding a conductor 211. The conductor 211 is electrically connected to the source of power through connector 194 which is mounted to the top of the cover 199 to permit electrical energization of the buffer solution 195.

The bottom buffer assembly 151 includes enclosed walls 201 defining a container for holding a buffer solution 203 and a cap 205 closing the container 201 and having a downwardly extending portion 213 extending into the buffer 203 for supporting a conductor 207 for applying energy to the bottom buffer solution 203. The gel sandwich 150 extends downwardly into the buffer solution 203 and upwardly into the buffer solution 195 to permit the electrical contact for electrophoresis.

Figure 12:
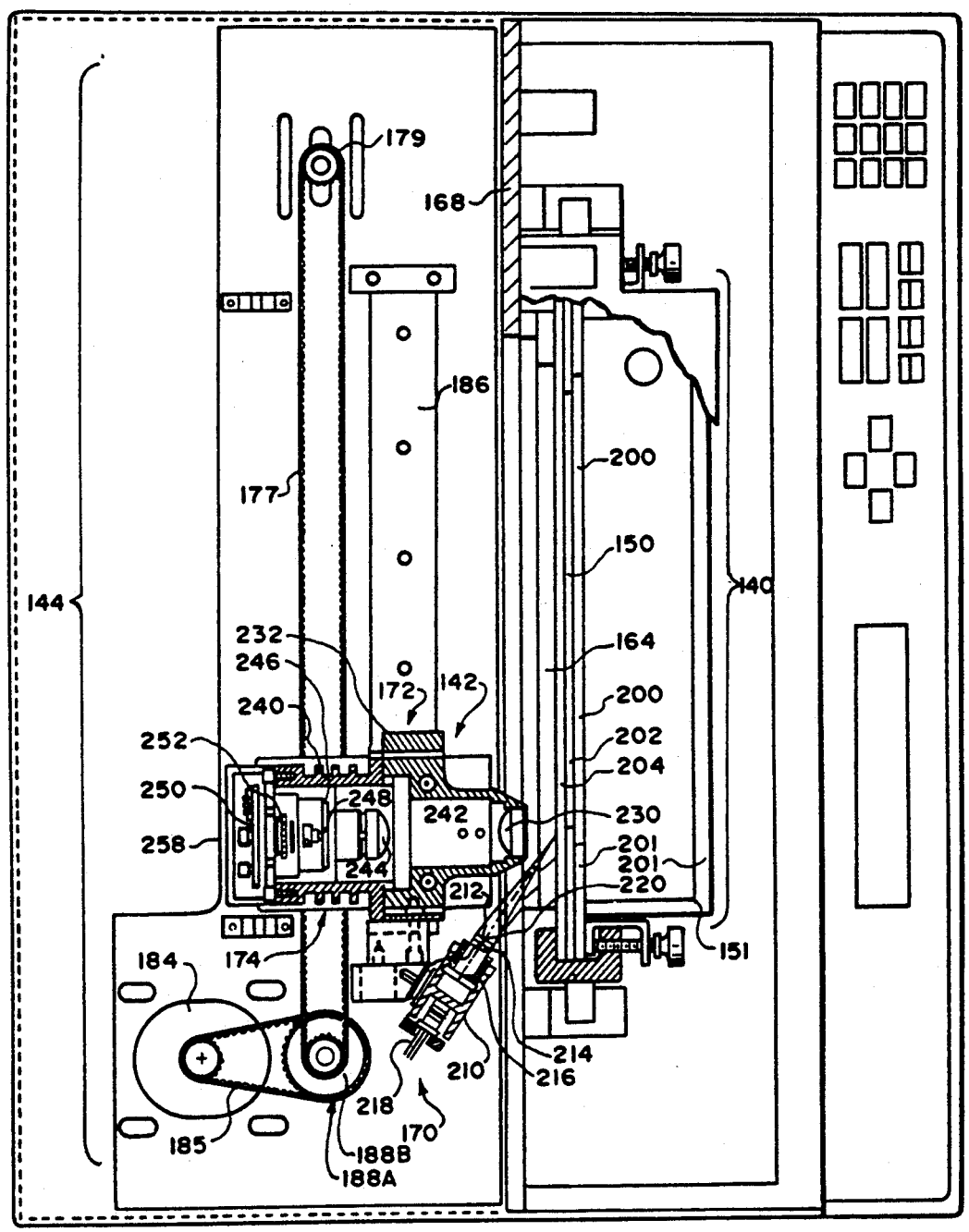
FIG. 12 is a sectional view of a portion of FIG. 10 taken through lines 12—12.

In FIG. 12, there is shown a sectional view taken through lines 12—12 of FIG. 10 showing the electrophoresis section 140, the scanning section 142 and the electrophoresis power supply section 144 mounted together to illustrate from a top view the arrangement of the apparatus support plate 168, the heater plate 164, the gel sandwich 150, a microscope assembly 172 and a photodiode assembly 174. The heater plate 164 and apparatus support plate 168 have slots running in a horizontal direction orthogonal to the lanes of DNA in the electrophoresis section 140 sized to receive the ends of a laser diode assembly 170 and the microscope section 172 for scanning thereof.

To cooperate with the separation and scanning of DNA bands, the gel sandwich 150 includes a front glass plate 200, a gel section 202 and a rear glass plate 204 mounted in contact with the heater plate 164 and having a section exposed for scanning by the laser diode assembly 170 and the microscope assembly 172. The rear glass plate 204 contacts the heater plate 164 and is separated from the front plate 200 by the gel section 202 within which DNA separation takes place.

To transmit light to the gel sandwich 150, the laser diode assembly 170 includes a housing 210, a focusing lens 212, a narrow band pass filter 214, a collimating lens 216 and a laser diode 218. The laser diode 218 emirs infrared or near infrared light which is collimated by the laser collimating lens 216 and filtered through the narrow band pass infrared filter 214. This light is focused by the focusing lens 212 onto the gel sandwich 150. Preferably, the point of focus on the gel section 202 of the gel sandwich 150 lies along or near the central longitudinal axis of the microscope section 172 and the photodiode section 174.

The thickness of the glass plates and the gel, the position of the laser and sensor and their angle of incidence are chosen, taking into consideration the refractive index of the gel and glass so that the light from the laser is absorbed by a maximum number of markers for one channel. The light from the laser is not directly reflected back because the angle of incidence to a normal is equal to the Brewster's angle at the first interface and is such as to impinge on the markers with full intensity after refraction but not be reflected by subsequent layers of the gel sandwich 150 into the sensor and the sensor views a large number of markers that fluoresce in a line of sight of substantial concentration.

To maintain temperature control over the laser diode, the housing 210: (a) is coupled to a heat sink through a thermal electric cooler 220, and (b) encloses the focusing lens 212, narrow band pass filter 214, collimating lens 216 and laser diode 218; and (c) accommodates the electrical leads for the diode.

To receive and focus light emitted by fluorescent markers from the gel section 202 in response to the light from the laser diode assembly 170, the microscope assembly 172 includes a collection lens 230, a housing 232 and a coupling section 234. The microscope assembly 172 is adapted to be positioned with its longitudinal axis centered on the collection lens 230 and aligned with the photodiode section 174 to which it is connected by the coupling section 234. For this purpose, the housing 232 includes a central passageway in which are located one or more optical filters with a band pass matching the emission fluorescence of the marked DNA strands along its longitudinal axis from the axis of the collection lens 230 to the coupling section 234 which transmits light to the photodiode section 174. With this arrangement, the collection lens 230 receives light from the fluorescent material within the gel section 202 and collimates the collected light for optical filtering and then transmission to the photodiode assembly 174.

To generate electrical signals representing the detected fluorescence, the photodiode assembly 174 includes a housing 240 having within it, as the principal elements of the light sensors, an inlet window 242, a focusing lens 244, a sapphire window 246 and an avalanche photodiode 248. To support the avalanche photodiode 248, a detector mounting plate 250 is mounted within the housing 240 to support a plate upon which the avalanche photodiode 248 is mounted. The inlet window 242 fits within the coupling section 234 to receive light along the longitudinal axis of the photodiode assembly 174 from the microscope assembly 172.

Within the housing 240 of the photodiode assembly 174, the sapphire window 246 and avalanche photodiode 248 are aligned along the common axis of the microscope assembly 172 and the photodiode assembly 174 and focuses light transmitted by the microscope assembly 172 onto a small spot on the avalanche photodiode 248 for conversion to electrical signals. A thermoelectric cooler 252 utilizing the Peltier effect is mounted adjacent to the detector mounting plate 250 to maintain a relatively cool temperature suitable for proper operation of the avalanche photodiode 248.

The lower buffer assembly 151 (FIG. 11) includes outer walls 201 and a bottom wall forming a compartment for buffer solution which encloses the bottom of the gel sandwich 150.

As best shown in this view, the stepping motor 184 rotates the belt 185 to turn the pulley 188A, which, in turn, rotates pulley 188B. The pulley 188B includes a belt 177 extending between it and an idler pulley 179 and attached at one location to the slideable support 186 to move the scanning microscope and laser lengthwise along the gel sandwich 150 for scanning purposes. The motor 184 by moving the carriage back and forth accomplishes scanning of the gel sandwich 150.

Figure 13:
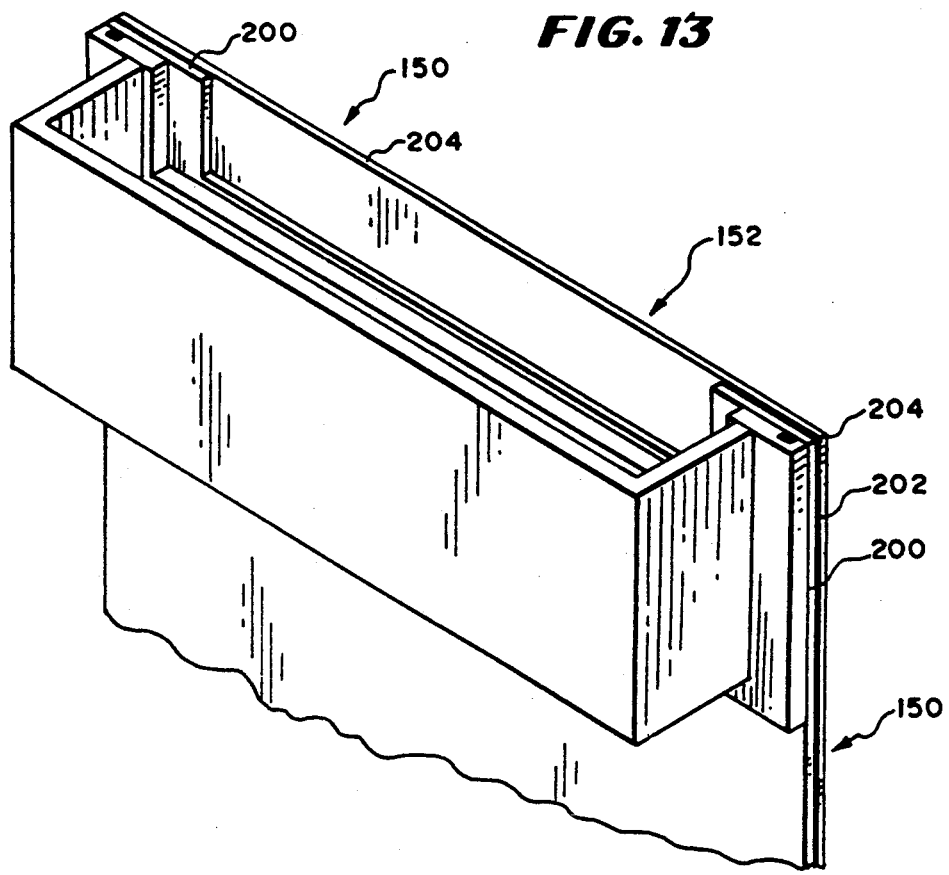
FIG. 13 is an exploded perspective view of a portion of the embodiment of FIG. 11.

In FIG. 13, there is shown a fragmentary perspective view of the gel sandwich 150 and the upper buffer assembly 152 mounted to each other showing the outer glass plate 200 cut away from the rear glass plate 204 to expose the gel section 202 to buffer solution within the upper buffer assembly 152. With this arrangement, samples may be pipetted between the glass plates 200 and 204 and moved downwardly by electrophoresis beyond the upper buffer assembly 152 and through the gel sandwich 150 to the bottom buffer (not shown in FIG. 13).

Figure 14:
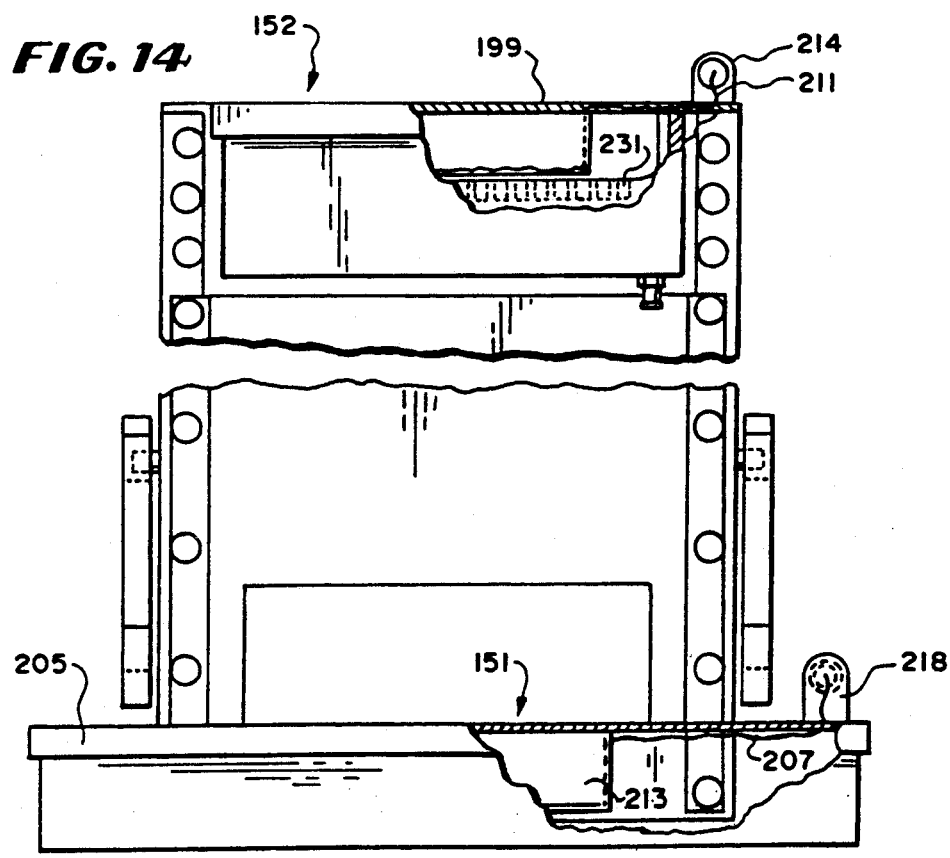
FIG. 14 is an enlarged view, partly broken away, of a portion of the embodiment of FIG. 11.

In FIG. 14, there is shown a broken away view of the gel sandwich 150 illustrating the upper buffer assembly 152 and the lower buffer assembly 151 connected to it at each end. As shown in this view, the cover 199 includes a connecting post 214 which receives the conductor 211 for connection to the downwardly extending portion of the cover 199 into the buffer compartment. Between the glass plates 200 and 204 (FIG. 13) of the gel sandwich 150, are a plurality of downwardly extending recesses 221 in the gel section 202 (FIG. 13) between the plates. DNA sample is pipetted into these recesses to form channels for electrophoresing to the lower buffer assembly 151.

To form an electical connection through the gel sandwich 150 from the upper buffer assembly 152 to the lower buffer assembly 151, a conducting post 216 is connected to the cover 205 of the lower buffer assembly 151 for receiving the conductor 207 which extends downwardly to the downwardly extended plate 213 and into the buffer solution.

Figure 15:
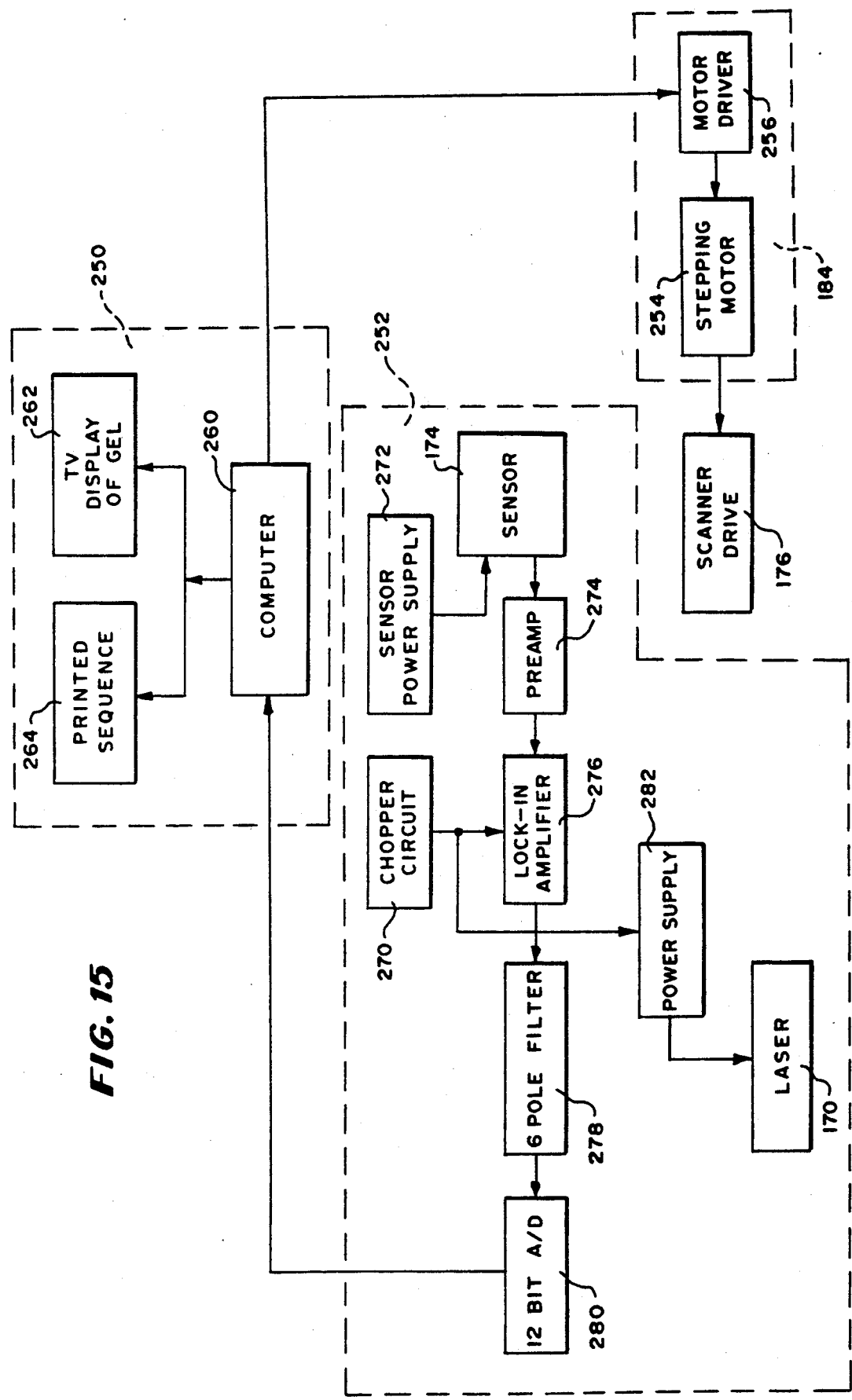
FIG. 15 is a block diagram of a circuit that may be used for coordination of a sensor, scanner drive and laser used in the embodiment of FIG. 9.

In FIG. 15, there is shown a block diagram of the circuitry used to control the remote station 122A of the embodiment of FIG. 11 having a control, correlation and readout section 250, the scanner drive 176, the motor assembly 184 for moving the scanner drive 176, and the sensing configuration 252. The sensing configuration 252 includes the laser assembly 170 and the sensor assembly 174 which receives signals, removes some noise, and transmits the signals for display and read out in the control, correlation and read out section 250 while the scanner drive 176 and motor for the scanner drive 184 receive signals from the control, correlation and read out section 250 to control the motion of the sensor back and forth across the gel sandwich. This overall configuration is not part of the invention of this application except insofar as it cooperates with the sensing configuration 252 to scan the DNA and determine its sequence in accordance with the embodiments of FIGS. 9-14.

To drive the sensor 174 from position to position, the motor assembly 184 includes a stepper motor 254 and a motor driver 256. The motor driver 256 receives signals from the control correlation and read-out section 250 and actuates the stepper motor 254 to drive the scanner drive 176. The scanner drive 176 is mechanically coupled to a stepping motor 254 through a belt and pulley arrangement for movement back and forth to sense the electrophoresis channels on the gel sandwich 150 (FIG. 12). The stepping motor 254 and driver circuitry 256 are convention and not themselves part of the invention.

The control, correlation and read out system 250 includes a computer which may be any standard microprocessor 260, a television display or cathode ray tube display 262 and a printer 264 for displaying and printing the results of the scans.

To sense data, the sensing configuration 252 includes in addition to the laser 170 and the sensor 174, a chopper circuit 270, a sensor power supply 272, a preamplifier 274, a lock-in amplifier 276, a 6-pole filter 278, a 12-bit analogue digital converter interface circuit 280 and a laser power supply 282.

The sensor 174 receives light from the laser 170 after it impinges upon the gel sandwich 150 (FIG. 12) and transmits the signals through preamplifier 274 to the lock-in amplifier 276. The sensor receives signals from the sensor power supply 272. The chopper circuit 270 provides pulses at synchronized frequencies to the lock-in amplifier 276.

The laser 170 receives power from the power supply 282 which is controlled by the chopper circuit 270 so that the signal from the laser is in synchronism with the signal applied to the lock-in amplifier 276 so that the output from the lock-in amplifier 276 to the 6-pole filter 278 discriminates against unwanted signal frequencies. This signal is converted to a digital signal in the 12-bit analogue to digital converter 280 which serves as an interface to the computer 260.

With this arrangement, the scanning rate may be set to discriminate against noise and the synchronized demodulation from the chopper control further reduces noise, particularly discriminating against the natural fluorescense of the glass in the gel sandwich 150 (FIGS. 11 and 12).

From the above description, it can be understood that the sequencing techniques of this invention have several advantages, such as: (1) they take advantage of resolution over time, as opposed to space; (2) they are continuous; (3) they are automatic; (4) they are capable of sequencing or identifying markers in relatively long strands including strands of more than 100 bases; and (5) they are relatively economical and easy to use.

While in the preferred embodiment, a single emission frequency is used in the infrared region in each channel and for all of A, T, G and C terminated strands with the channel location identifying the terminating base type, multiple fluorescent markers can be used with the wavelength being used to identify the base type. In such an embodiment, an optical means detects a plurality of wavelengths and the computer correlates intensity data, corresponding lanes and corresponding wavelengths.

Although a preferred embodiment of the invention has been described with some particularity, many modifications and variations are possible in the preferred embodiment within the light of the above description. Accordingly, within the scope of the appended claims, the invention may be practiced other than as specifically described.

What is claimed is:

1. A method for sequencing DNA comprising:
   applying flourescently marked DNA samples at a plurality of locations for electrtophoresing in a plurality of channels through a gel electrophoresis slab;
   establishing electrical potential across said gel electrophoresis slab wherein DNA samples are resolved in accordance with the size of DNA fragments in said gel electrophoresis slab into fluorescently marked DNA bands;
   scanning the separated sampled photoelectrically with a laser and a sensor wherein the laser scans with scanning light at a scanning light frequency within the absorbance spectrum of said fluorescently marked DNA samples and sensing light at the emission frequency of the marked DNA;
   modulating said light from said laser at a predetermined modulation frequency;
   detecting fluorescent light emitted by said DNA bands at said modulation frequency, whereby background noise from the medium through which the light is transmitted may be discriminated against;
   said step of modulating including the step of modulating said light at a frequency with the band between 100 hertz to 30 kilohertz.

2. A method of DNA sequencing comprising the steps of:
   applying opposite polarity electrical potentials to a first and at least second buffer;
   applying fluorescently marked DNA strands to a plurality of channels of gel, whereby said fluorescently marked DNA is electrophoresced along said gel so that the bands of the more mobile strands in at least one channel is fully resolved while some of the less mobile strands to be later formed into bands are unresolved in a continuous process;
   scanning across said channels with light emitted from a diode laser;
   detecting fluorescent light emitted by said fluorescently marked strands, whereby the time sequence of separated bands may be obtained;
   said step of detecting including the step of scanning across said channels with a microscope focused on the bands receiving said light.

3. A method according to claim 2 wherein said microscope and diode laser are moved together across said channels to perform said scanning.

4. A method according to claim 2 wherein the light rom the diode laser is scanned at an angle chosen to impinge on the bands with full intensity after refraction but not be reflected into the microscope.

5. A method according to claim 4 wherein the light from the diode laser is scanned at an angle to the surface being scanned equal to the Brewster's angle.

6. A method of DNA sequencing comprising the steps of:
   applying opposite polarity electrical potentials to a first and at least second buffer;
   applying fluorescently marked DNA strands to a plurality of channels of gel, whereby said fluorescently marked DNA is electrophoresced along said gel so that the bands of the more mobile strands in at least one channel is fully resolved while some of the less mobile strands to be later formed into bands are unresolved in a continuous process;
   scanning across said channels with light emitted from a laser; and
   detecting fluorescent light emitted by said fluorescently marked strands, whereby the time sequence of separated bands may be obtained, wherein the light from said laser is in the band incorporating at least the near infrared and infrared regions and said detector responds to light in a band including at least said near infrared and infrared regions.

7. Apparatus for sequencing DNA comprising:
   a gel electrophoresis slab;
   means for establishing electrical potential across gel electrophoresis slab;
   means for applying DNA samples at a plurality of locations for electrophoresing in a plurality of channels through said gel electrophoresis slab;
   means for separating DNA samples in accordance with the size of DNA fragments in said gel electrophoresis slab;
   means for scanning the separated samples photoelectrically;
   said means for scanning including a laser, a microscope, and a sensor;
   a modulator means positioned between said laser and said gel electrophoresis slab for modulating light at a pulse rate between 100 hertz to 30 kilohertz;
   a detector being positioned to absorb fluorescent light emitted by said DNA bands;

said sensor being applied to means for detecting pulses of light having the same pulse rate as laser light pulses, whereby background noise from the medium through which it is applied is discriminated against.

8. DNA sequencing apparatus comprising:
gel electrophoresis means;
one end of said gel electrophoresis means communicating with a buffer solution;
at least one other side of said gel electrophoresis means communicating with a second buffer solution;
means for applying opposite polarity electrical potentials to said first and at least second buffer;
means for applying fluorescently marked DNA strands to a a plurality of channels of said gel, whereby said fluorescently marked DNA is electrophoresed along said gel so that the bands of the more mobile strands in at least one channel is fully resolved while some of the less mobile strands to be later formed into bands are unresolved in a continuous process;
means for scanning across said channels with light emitted from a diode laser;
means for detecting fluorescent light emitted by said fluorescently marked strands, whereby the time sequence of separated bands may be obtained;
said means for detecting including means for scanning across said channels with a microscope focussed on the bands receiving said light.

9. DNA sequencing apparatus according to claim 8 further including means for moving said microscope and diode laser together across said channels to perform said scanning.

10. DNA sequencing apparatus according to claim 8 wherein the light from the diode laser is scanned at an angle chosen to impinge on the bands with full intensity after refraction but not be reflected into the microscope.

11. DNA sequencing apparatus according to claim 10 wherein the light from the diode laser is scanned at an angle to the surface being scanned equal to the Brewster's angle.

12. DNA sequencing apparatus comprising:
gel electrophoresis means;
one end of said gel electrophoresis means communicating with a buffer solution;
at least one other side of said gel electrophoresis means communicating with a second buffer solution;
means for applying opposite polarity electrical potentials to said first and at least second buffer;
means for applying fluorescently marked DNA strands to a plurality of channels of said gel, whereby said fluorescently marked DNA is electrophoresed along said gel so that the bands of the more mobile strands in at least one channel are fully resolved while some of the less mobile strands to be later formed into bands are unresolved in a continuous process;
means for scanning across said channels with light emitted from a laser;
means for detecting fluorescent light emitted by said fluorescently marked strands, whereby the time sequence of separated bands may be obtained;
said means for scanning emitting including means for scanning with light from said laser in a band incorporating at least the near infrared and infrared regions;
said detector being responsive to light in a band of wavelengths including at least said near infrared and infrared regions.

* * * * *